US009381098B2

(12) United States Patent
Gittings et al.

(10) Patent No.: US 9,381,098 B2
(45) Date of Patent: Jul. 5, 2016

(54) TOOL SYSTEMS FOR IMPLANTING PROSTHETIC INTERVERTEBRAL DISCS

(75) Inventors: Darin C. Gittings, Sunnyvale, CA (US); Frank Fellenz, Los Gatos, CA (US); Jeffrey J. Dolin, Belmont, CA (US); Janine C. Robinson, Half Moon Bay, CA (US); Daren L. Stewart, Belmont, CA (US)

(73) Assignee: SPINAL KINETICS, Inc., Sunnyvale, CA (US)

( * ) Notice: Subject to any disclaimer, the term of this patent is extended or adjusted under 35 U.S.C. 154(b) by 1483 days.

(21) Appl. No.: 11/529,824

(22) Filed: Sep. 28, 2006

(65) Prior Publication Data

US 2008/0082169 A1    Apr. 3, 2008

(51) Int. Cl.
*A61F 2/44* (2006.01)
*A61F 2/46* (2006.01)
(Continued)

(52) U.S. Cl.
CPC .............. *A61F 2/4684* (2013.01); *A61B 17/025* (2013.01); *A61B 17/1604* (2013.01); *A61B 17/1606* (2013.01); *A61B 17/1671* (2013.01); *A61F 2/4611* (2013.01); *A61F 2/4657* (2013.01); *A61B 17/1735* (2013.01); *A61B 17/92* (2013.01); *A61B 19/54* (2013.01); *A61B 2017/0256* (2013.01); *A61B 2019/303* (2013.01); *A61B 2019/461* (2013.01); *A61B 2019/467* (2013.01); *A61F 2002/3008* (2013.01); *A61F 2002/30507* (2013.01); *A61F 2002/30538* (2013.01); *A61F 2002/30553* (2013.01);

(Continued)

(58) Field of Classification Search
CPC ........... A61F 2/44–2/4495; A61F 2/46; A61F 2/4611
USPC ................. 606/86 A, 99–100, 279, 280–299, 606/70–71; 623/17.11–17.16
See application file for complete search history.

(56) References Cited

U.S. PATENT DOCUMENTS

| 3,867,728 A | 2/1975 | Stubstad et al. |
| 4,309,777 A | 1/1982 | Patil |

(Continued)

FOREIGN PATENT DOCUMENTS

WO    WO2005/011523    2/2005

OTHER PUBLICATIONS

Hudgins, Robert, "Development and Characterization of a Prosthetic Intevertebral Disc," Thesis presented to the Academic Faculty, Georgia Institute of Technology (Nov. 98).

(Continued)

*Primary Examiner* — Matthew Lawson
(74) *Attorney, Agent, or Firm* — E. Thomas Wheelock

(57) ABSTRACT

Described are tools—including distractor, trial, chisel, and inserter—that may be used as a system for implanting a prosthetic intervertebral disc in a spine. The distractor moves vertebrae and may have angled forks optionally offset for visibility with removable jaws optionally matching desired lordotic angles. The trial tool(s) may fit within the distractor forks, include a lordotic angle, and may include a disc portion, an adjustable stop, and a feature to control movement of the disc portion relative to the adjustable stop. The chisel tool cuts grooves in the vertebral bodies, which grooves affix the disc to the vertebrae. The chisel(s) may fit within openings in the trial, where those openings also serve as a guide during the groove-cutting step. The inserter tool, optionally with a movable pusher, is used for inserting the prosthetic disc into the prepared intervertebral disc space.

23 Claims, 47 Drawing Sheets

(51) Int. Cl.
  *A61B 17/02* (2006.01)
  *A61B 17/16* (2006.01)
  *A61B 17/17* (2006.01)
  *A61B 17/92* (2006.01)
  *A61B 19/00* (2006.01)
  *A61F 2/30* (2006.01)

(52) U.S. Cl.
  CPC .............. *A61F2002/30563* (2013.01); *A61F 2002/30579* (2013.01); *A61F 2002/30601* (2013.01); *A61F 2002/30616* (2013.01); *A61F 2002/30884* (2013.01); *A61F 2002/4627* (2013.01); *A61F 2002/4628* (2013.01); *A61F 2002/4658* (2013.01); *A61F 2002/4668* (2013.01); *A61F 2220/0025* (2013.01); *A61F 2250/0006* (2013.01); *A61F 2250/0008* (2013.01); *A61F 2250/0098* (2013.01)

(56) References Cited

U.S. PATENT DOCUMENTS

| | | | | |
|---|---|---|---|---|
| 4,623,574 | A | 11/1986 | Harpell et al. | |
| 4,759,769 | A | 7/1988 | Hedman et al. | |
| 4,911,718 | A | 3/1990 | Lee et al. | |
| 4,932,969 | A | 6/1990 | Frey et al. | |
| 4,997,432 | A * | 3/1991 | Keller | 623/17.11 |
| 5,002,576 | A | 3/1991 | Fuhrmann et al. | |
| 5,039,519 | A | 8/1991 | Inoue et al. | |
| 5,171,281 | A | 12/1992 | Parsons et al. | |
| 5,221,431 | A | 6/1993 | Choe et al. | |
| 5,221,432 | A | 6/1993 | Choe et al. | |
| 5,314,477 | A * | 5/1994 | Marnay | 623/17.15 |
| 5,370,697 | A * | 12/1994 | Baumgartner | 623/17.15 |
| 5,456,722 | A | 10/1995 | McLeod et al. | |
| 5,458,642 | A | 10/1995 | Beer et al. | |
| 5,545,229 | A | 8/1996 | Parsons et al. | |
| 5,609,634 | A | 3/1997 | Voydeville | |
| 5,702,450 | A * | 12/1997 | Bisserie | 623/17.16 |
| 5,827,328 | A | 10/1998 | Buttermann | |
| 6,063,121 | A | 5/2000 | Xavier et al. | |
| 6,113,638 | A | 9/2000 | Williams et al. | |
| 6,156,067 | A | 12/2000 | Bryan et al. | |
| 6,258,125 | B1 | 7/2001 | Paul et al. | |
| 6,264,695 | B1 | 7/2001 | Stoy | |
| 6,402,785 | B1 | 6/2002 | Zdeblick et al. | |
| 6,419,704 | B1 | 7/2002 | Ferree | |
| 6,419,706 | B1 | 7/2002 | Graf | |
| 6,436,137 | B2 | 8/2002 | Wang et al. | |
| 6,447,543 | B1 | 9/2002 | Studer et al. | |
| 6,527,803 | B1 | 3/2003 | Crozet et al. | |
| 6,527,804 | B1 | 3/2003 | Gauchet et al. | |
| 6,533,818 | B1 | 3/2003 | Weber et al. | |
| 6,582,466 | B1 | 6/2003 | Gauchet | |
| 6,582,468 | B1 | 6/2003 | Gauchet | |
| 6,592,624 | B1 * | 7/2003 | Fraser et al. | 623/17.16 |
| 6,626,943 | B2 | 9/2003 | Eberlein et al. | |
| 6,626,944 | B1 | 9/2003 | Taylor | |
| 6,645,248 | B2 | 11/2003 | Casutt | |
| 6,656,224 | B2 | 12/2003 | Middleton | |
| 6,682,562 | B2 | 1/2004 | Viart et al. | |
| 6,692,495 | B1 | 2/2004 | Zacouto | |
| 6,726,721 | B2 | 4/2004 | Stoy et al. | |
| 6,733,533 | B1 | 5/2004 | Lozier | |
| 6,733,535 | B2 | 5/2004 | Michelson | |
| 6,746,485 | B1 | 6/2004 | Zucherman et al. | |
| 6,749,635 | B1 | 6/2004 | Bryan | |
| 6,755,841 | B2 * | 6/2004 | Fraser et al. | 606/99 |
| 6,827,740 | B1 | 12/2004 | Michelson | |
| 6,827,743 | B2 | 12/2004 | Eisermann et al. | |
| 6,981,989 | B1 * | 1/2006 | Fleischmann et al. | 623/17.11 |
| 7,025,787 | B2 | 4/2006 | Bryan et al. | |
| 7,060,097 | B2 | 6/2006 | Fraser et al. | |
| 7,074,240 | B2 | 7/2006 | Pisharodi | |
| 7,118,580 | B1 * | 10/2006 | Beyersdorff et al. | 606/99 |
| 7,147,665 | B1 | 12/2006 | Bryan | |
| 7,166,130 | B2 | 1/2007 | Ferree et al. | |
| 7,169,182 | B2 * | 1/2007 | Errico et al. | 623/17.15 |
| 7,204,852 | B2 * | 4/2007 | Marnay et al. | 623/17.16 |
| 7,220,282 | B2 | 5/2007 | Kuslich | |
| 7,229,441 | B2 | 6/2007 | Trieu et al. | |
| 7,291,150 | B2 | 11/2007 | Graf | |
| 7,294,134 | B2 * | 11/2007 | Weber | 606/99 |
| 7,309,357 | B2 | 12/2007 | Kim et al. | |
| 7,320,689 | B2 * | 1/2008 | Keller | 606/99 |
| 2002/0026244 | A1 | 2/2002 | Trieu | |
| 2002/0111687 | A1 | 8/2002 | Ralph et al. | |
| 2002/0128714 | A1 | 9/2002 | Manasas et al. | |
| 2003/0028251 | A1 | 2/2003 | Mathews | |
| 2003/0055503 | A1 * | 3/2003 | O'Neil | 623/17.11 |
| 2004/0006343 | A1 | 1/2004 | Sevrain | |
| 2004/0143332 | A1 | 7/2004 | Krueger et al. | 623/17.14 |
| 2004/0215198 | A1 * | 10/2004 | Marnay et al. | 606/86 |
| 2004/0220582 | A1 * | 11/2004 | Keller | 606/99 |
| 2004/0225295 | A1 * | 11/2004 | Zubok et al. | 606/90 |
| 2004/0243240 | A1 * | 12/2004 | Beaurain et al. | 623/17.14 |
| 2005/0021042 | A1 * | 1/2005 | Marnay et al. | 606/99 |
| 2005/0021146 | A1 | 1/2005 | de Villiers et al. | |
| 2005/0033437 | A1 * | 2/2005 | Bao et al. | 623/17.15 |
| 2005/0055029 | A1 * | 3/2005 | Marik et al. | 606/87 |
| 2005/0060036 | A1 | 3/2005 | Schultz et al. | |
| 2005/0119665 | A1 * | 6/2005 | Keller | 606/99 |
| 2005/0131542 | A1 * | 6/2005 | Benzel et al. | 623/17.13 |
| 2005/0216084 | A1 * | 9/2005 | Fleischmann et al. | 623/17.11 |
| 2005/0283244 | A1 * | 12/2005 | Gordon et al. | 623/17.15 |
| 2006/0058808 | A1 * | 3/2006 | Schneid | 606/99 |
| 2006/0064107 | A1 * | 3/2006 | Bertagnoli et al. | 606/99 |
| 2006/0129239 | A1 | 6/2006 | Kwak | |
| 2006/0149382 | A1 * | 7/2006 | Lamprich et al. | 623/17.13 |
| 2006/0235535 | A1 * | 10/2006 | Ferree et al. | 623/17.16 |
| 2007/0032875 | A1 | 2/2007 | Blacklock et al. | |
| 2007/0100453 | A1 * | 5/2007 | Parsons et al. | 623/17.14 |
| 2007/0100456 | A1 * | 5/2007 | Dooris et al. | 623/17.14 |
| 2007/0123985 | A1 * | 5/2007 | Errico et al. | 623/17.11 |
| 2007/0129806 | A1 * | 6/2007 | Harms et al. | 623/17.13 |
| 2007/0168033 | A1 | 7/2007 | Kim et al. | |
| 2008/0109081 | A1 * | 5/2008 | Bao et al. | 623/17.15 |

OTHER PUBLICATIONS

Takahata et al. "Bone Ingrowth Fixation of Artificial Intervertebral Disc Consisting of Bioceramic-coated Three-dimensional Fabric," SPINE, vol. 28, No. 7, pp. 637-644.

* cited by examiner

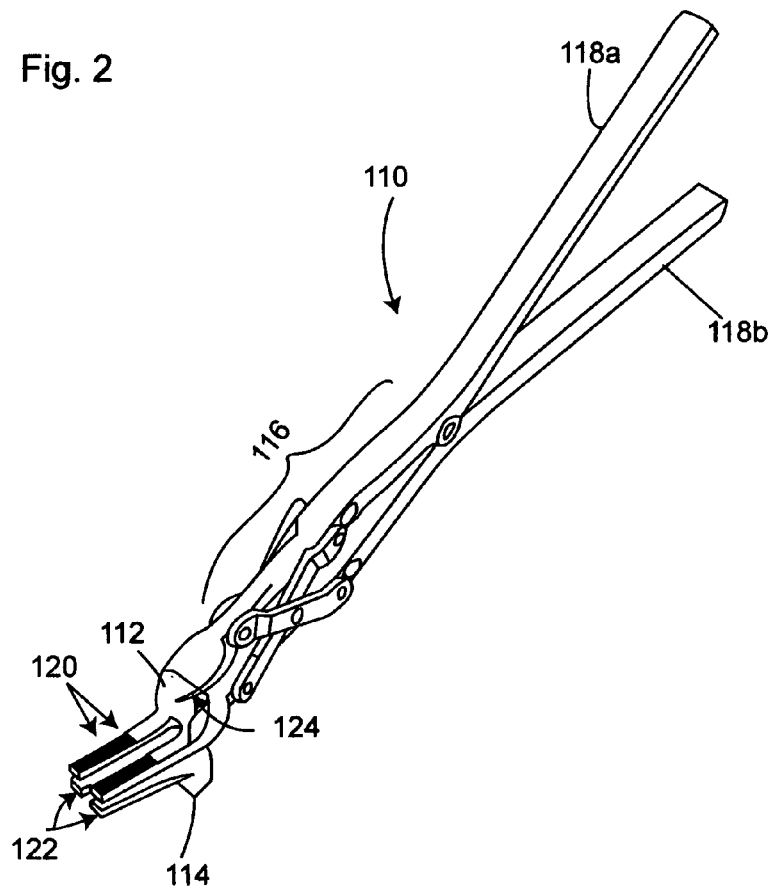

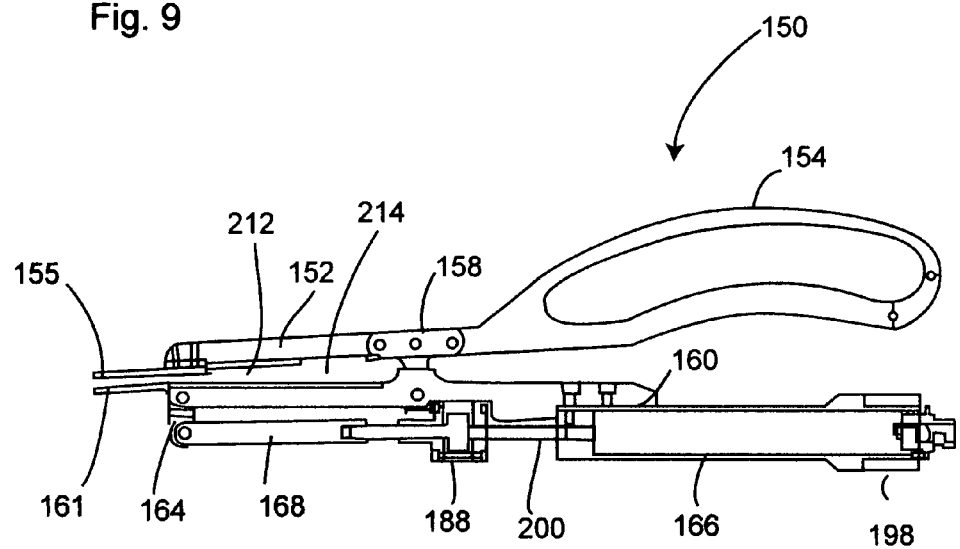

TOOL SYSTEMS FOR IMPLANTING PROSTHETIC INTERVERTEBRAL DISCS

FIELD

This description provides for various tools and tool systems that may be used for introducing a prosthetic intervertebral disc as a replacement for a natural disc in a spine.

BACKGROUND

The intervertebral or spinal disc is an anatomically and functionally complex joint. The intervertebral disc is made up of three component structures: (1) the nucleus pulposus; (2) the annulus fibrosus; and (3) the vertebral end plates. The biomedical composition and anatomical arrangements within these component structures are related to the biomechanical function of the disc.

The spinal disc may be displaced or damaged due to trauma or disease. As a result of such displacement or damage, the nucleus pulposus may herniate and protrude into the vertebral canal or intervertebral foramen. Such a deformation is known as a herniated or "slipped" disc. This protrusion may press upon one or more of the spinal nerves exiting the vertebral canal through a partially obstructed foramen, thereby causing pain or paralysis in the area of its distribution. Similarly, spinal discs may degenerate with age or excessive use resulting in a decrease in disc height. One specific result of such disc height decline is the narrowing of the foramenal space, often causing pressure on the emanating nerve and causing pain and paralysis in the area of the nerve's influence. Pressure on the nerve and disc herniation often happen together.

Artificial intervertebral discs are used to replace damaged or diseased natural intervertebral discs. Various types of artificial intervertebral discs have been developed with the goal of restoring the normal kinematics and load-sharing properties of the natural intervertebral discs. Two such types are ball-and-socket joint type discs and the elastomer type discs.

We have described prosthetic intervertebral discs in application Ser. No. 10/903,276, titled "Prosthetic Intervertebral Disc and Methods for Using Same," filed on Jul. 30, 2004, assigned to Spinal Kinetics Inc., the entirety of which is incorporated by reference.

SUMMARY

Below, we describe tools and systems of tools variously for determining the proper size and position of a prosthetic disc to be implanted, for chiseling a site for the placement of the prosthetic intervertebral discs, and for implanting those discs. We also describe suitable prosthetic discs, those generally including a first end plate, a second end plate, and a compressible core member positioned between the first and second end plates. The prosthetic disc may also include attachment subcomponents or features extending from or integral with one or both of the end plates for affixing the disc to the vertebral bodies.

The tool systems used for implanting prosthetic intervertebral discs may include a distractor, various trials, various chisels, and an inserter.

The distractor is used for moving or "distracting" two adjacent vertebral bodies in a spine thereby providing access to a space for implanting the prosthetic disc. One variation of the distractor is made up of an upper jaw, a lower jaw, a mechanism for opening the upper and lower jaws, and a mechanism for maintaining the opening between the upper and lower jaws. Each jaw includes at least one fork used to contact one of the vertebrae to be distracted. In another variation of the distractor, the upper and lower forks are angled relative to each other to match a natural lordotic angle between selected vertebral bodies. The jaws may be removable from the distractor and those removable jaws may be configured to match different lordotic angles found between adjacent vertebrae in the spine. The upper and lower forks may be offset and angled from the longitudinal center axis of the distractor to allow the user to better see enjoy better access to the disc space.

The distractor may also include an adjustable measuring feature thereby allowing the distractor both to distract adjacent vertebral bodies and also to measure the height and lordotic angle of the disc space. This variation of the distractor may include at least one fixed fork and at least one adjustable fork and an adjustment mechanism for changing the angle of the adjustable fork relative to the fixed fork. This adjustment feature may be used to measure the lordotic angle between the vertebral bodies.

The distractor may be configured so that the forks distract the vertebral bodies in response to squeezing two handles on the distractor. The distance between the ends of the two handles may be used to indicate the distance that the forks have opened, and therefore, to display the height of the disc space.

Another tool that may be included in our various tool systems is the trial. Multiple trials may be included in the tool systems. Trials are individual tools used to determine the size and the position of the prosthetic intervertebral disc to be implanted. In essence, a trial is inserted into a disc space to assure correspondence between the size and shape of the disc space and the size and shape of the prosthetic disc.

In one variation of the trial design, each trial has recesses that are dimensioned to allow the trial to be positioned within the distractor forks. This feature allows the trial to be inserted into the disc space by advancing between the distractor forks, which feature allows the selected trial both to provide its "trial" size and shape data and to prevent the trial from "over-distracting" the disc space. The trial may have a lordotic shape to match the lordotic angle between the selected vertebral bodies.

The trial may include a disc portion, an adjustable stop, and a lead screw, or other mechanism, connected between the disc portion and adjustable stop configured to provide controlled movement of the disc portion relative to the adjustable stop. Optionally, the trial may be releasable from its handle.

The trial may include at least one retractable foot with an extendible, roughened surface useful as a "traction" feature for the trial. When the trial is in the disc space, the retractable foot is raised from a surface of the trial to engage a surface on the vertebral bodies. The roughened surface of the foot provides increased traction between the trial and the vertebral body. Various surface types may also be used to provide increased traction. To remove the trial from the disc space, the retractable foot is retracted back into the trial.

The trials may be radiolucent but have radio-opaque features, such as alignment pins, for indicating AP depth and lateral alignment of the trial between the vertebral bodies. Similarly, the trials may be radio-opaque with radiolucent openings for aiding with alignment.

The next members of the tool system are chisels. One or more chisels may be used to cut grooves in the vertebral bodies, which grooves are, in turn, used for affixing the disc to the vertebral bodies. The chisels may include cutters for creating the grooves. The number, orientation, and shape of the cutters may match the attachment component of the prosthetic disc to be implanted. The size of the cutters may be a percentage of the size—in width, height, or both—of the attachment component on the disc, ranging anywhere from 50-125%, and preferably approximately 80%. The chisel or chisels may be configured to enter openings or recesses in the trial, where those openings or recesses are sized to serve as a guide during the groove-cutting step. The chisels may include "stops" that contact, for instance, a surface on the exterior of the trial when the chisel is inserted into the trial at a predetermined depth. That stop is used to control the length of a groove cut by the chisel in the disc space. The chisels may be serially inserted into the trial or may be inserted simultaneously into the trial.

The chisels may be wholly or partially radio-opaque, if desired, so that a user may visualize those chisels under fluoroscopy to ensure correct positioning, both laterally and anterior-posteriorly.

Next, the inserter tool is used for inserting the prosthetic disc into the disc space between the vertebral bodies. The inserter may include engagement features configured to cooperate with mating features on the prosthetic disc's end plates. Those inserter engagement features and prosthetic disc mating features may be arranged so that, when the disc is inserted into its selected disc space, the prosthetic disc itself is in a compressed, hyper-lordotic state that eases that final implantation passage.

The inserter may also include a movable mechanism (or "pusher") for separating the prosthetic disc from the inserter by pushing the inserter away from the then-implanted disc.

Optionally, a compression vice may be included for the purpose of temporarily squeezing or conforming the prosthetic disc and holding it in that temporary configuration as the disc is placed in the inserter.

All or parts of the above instruments may be radiolucent or radio-opaque, as desired, to facilitate visualization of the instruments under fluoroscopy.

Procedures

We also describe methods for implanting the prosthetic disc between the vertebral bodies.

First, the natural disc between the vertebral bodies is removed. The distractor may then be used to increase the resulting disc space between the vertebral bodies. For instance, the upper and lower distractor forks may then be inserted between the vertebral bodies and opened to distract the vertebral bodies. If the distractor variation having angled upper and lower forks is used to determine and to match the lordotic angle between the vertebral bodies, the distraction step may include the step of inserting the properly angled upper and lower distractor forks between the vertebral bodies. The centerline of the vertebral bodies may be marked on the vertebral bodies. A centerline mark on the distractor may be then aligned with the centerline of the vertebral bodies to center the distractor forks.

A progression of different sized trials may then be inserted into the disc space to determine the appropriate size, including height, lordotic angle, anterior-posterior and lateral dimensions, and the position of the prosthetic disc to be implanted. The different sized trials may have shapes corresponding to different lordotic angles and sizes.

In one variation, a trial may be inserted between the distractor forks while the distractor forks reside in the disc space. In this variation, the distractor forks recessed into the trial prevent or limit the trial insertion from "over-distracting" the disc space by providing boundaries on the upper and lower surfaces of the trial.

Further, for the variation in which the distractor forks are centered with the centerline of the vertebral bodies, the forks serve as a guide that centers the trial with the centerline of the vertebral bodies. An adjustable trial stop may be butted against the anterior surface of the trial. A portion of the trial may then be controllably moved relative to the adjustable stop to adjust the anterior-posterior (AP) depth of the disc portion of the trial in the disc space. In some variations, the AP depth of the disc portion of the trial may be adjusted by turning a handle attached to the trial. Where such an optional rotational adjustment on the trial handle is included, the rotation results in a depth adjustment that is proportional to rotation allowing the AP depth of the disc portion may be blindly adjusted. The trial may also have radio-opaque indicators allowing for visualization of the trial position with fluoroscopy.

After the trial is at a desired AP depth, the distractor may then be removed from the disc space and the chisel or chisels used to cut grooves in the vertebral bodies. If the chisel includes an upper chisel head that is to be slid into upper trial recesses and a lower chisel head that is to be received into the lower recesses in the trial, the grooves may be cut by introducing those chisels in sequence.

In one variation, a first chisel head is inserted into a trial; a cutter, e.g., blade, on that chisel head is driven into one of the vertebral bodies perhaps with a hammer, to cut grooves into the vertebral body. The chisel is driven until a stop on the chisel head engages a surface of the trial. This indicates that the chisel head has progressed to a specific chosen depth in the trial and, therefore, the chosen length of groove in the vertebral body. That length is chosen to match a corresponding measurement on the prosthetic disc attachment component.

That first chisel head may be left completely or partially in the disc space while another chisel head is inserted into another guide opening in the trial to cut additional grooves into an adjoining vertebral body. The other chisel head may also include a stop for controlling the length of the groove. If the cutters of the first chisel head are left in the first groove, they serve as anchors and spacers to prevent movement of the trial as the second chisel head is driven into the adjacent vertebral body. This procedure helps to ensure that the grooves in the two vertebral bodies are properly aligned for placement of the prosthetic disc.

If the procedure involves the use of a trial shape that matches the lordotic angle between the adjacent vertebral bodies, the cutting step may involve guiding the chisel heads through recesses in the trial so that the grooves are cut at the correct lordotic angle and at a uniform depth. After the grooves are cut, each chisel head is removed from the disc space, e.g., using a slide hammer.

The trial is then removed from the disc space and the prosthetic disc is inserted and positioned in that disc space using the inserter. The prosthetic disc may be placed in the inserter by matching engagement features on the inserter with cooperating features on the prosthetic disc. The engagement and mating features may be arranged so that the prosthetic disc is compressed to a hyper-lordotic, state and then placed on the inserter. When the disc is compressed into a hyper-lordotic state, the disc may be eased into the disc space between the vertebral bodies. The prosthetic disc may be so-compressed and held in a compression vice during placement in the inserter. After the prosthetic disc is positioned in the disc space, the prosthetic disc may be then released from the inserter. The prosthetic disc may be released from the inserter by pushing the inserter away from the prosthetic disc using a movable pusher.

Other and additional devices, apparatus, structures, and methods are described by reference to the drawings and detailed description below.

BRIEF DESCRIPTION OF THE FIGURES

The Figures are not necessarily drawn to scale, with some components and features being exaggerated for clarity.

FIG. 2 is a perspective view of a distractor that includes upper and lower jaws with forks for distracting two adjacent vertebral bodies.

FIG. 9 provides a cross-sectional side view of the adjustable measuring distractor.

DESCRIPTION

Many variations of our cooperative disc implantation tools include a distractor, one or more trials, one or more chisels, and an inserter. The set of tools is useful in implanting a prosthetic intervertebral disc between adjacent vertebral bodies.

Figure 1A:
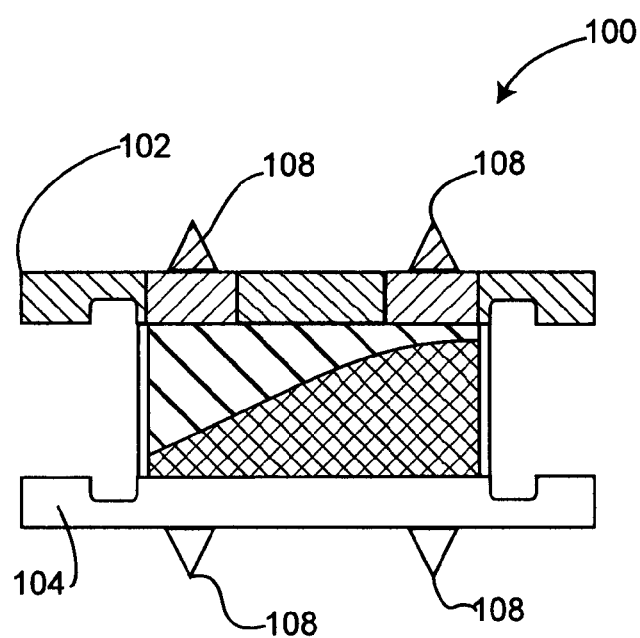
FIG. 1A is a partial cutaway, front view of a prosthetic disc suitable for implantation using the tools and tools systems described herein.

FIG. 1A shows a partial cutaway, side view of an example of a prosthetic disc (100) that may be implanted between adjacent vertebral bodies using our implantation tools. The depicted prosthetic disc (100) includes an upper end plate (102), a lower end plate (104), and a compressible core member (106) between the upper and lower end plates (102, 104). The prosthetic disc (100) may be configured to mimic the functional characteristics of a natural intervertebral disc. The depiction of prosthetic disc (100) also includes anchor fins (108) (serving as attachment components) extending from the upper and lower end plates (102, 104). As explained below, the anchor fins (108) fit into grooves cut in the adjacent vertebral bodies for affixing the prosthetic disc (100) to those vertebrae. A more detailed discussion on prosthetic discs may be found in U.S. application Ser. No. 10/903,276, titled "Prosthetic Intervertebral Disc and Methods for Using Same," filed on Jul. 30, 2004, the entire specification of which is incorporated herein by reference. Other types of prosthetic discs may also be implanted using the devices and methods described herein.

Turning to FIGS. 2-5, the distractor (110) is used to distract (or to separate) adjacent vertebral bodies to create a disc space into which the prosthetic disc is to be implanted. This variation of the distractor (110) includes an upper jaw (112), a lower jaw (114), and an assembly (116) for opening the jaws (112, 114) by squeezing two distractor levers (118a, 118b) together. Each jaw (112, 114) may include two fork tines (120, 122), respectively, each tine pair forming a fork for engaging one of the vertebral bodies to be separated. Alternatively, one or both jaws may include one to four fork tines, perhaps between two to three fork tines. The surfaces of the fork tines (120, 122) engaging the vertebral bodies are shown to be roughened, e.g., by knurling, or incorporating ridges, grooves, bumps, lumps, or the like to increase traction or grip with the vertebral bodies. The distractor (110) is further depicted to include a centerline mark (124) or indicator for centering the forks with the centerline of the vertebral bodies, as explained below.

Figure 3:
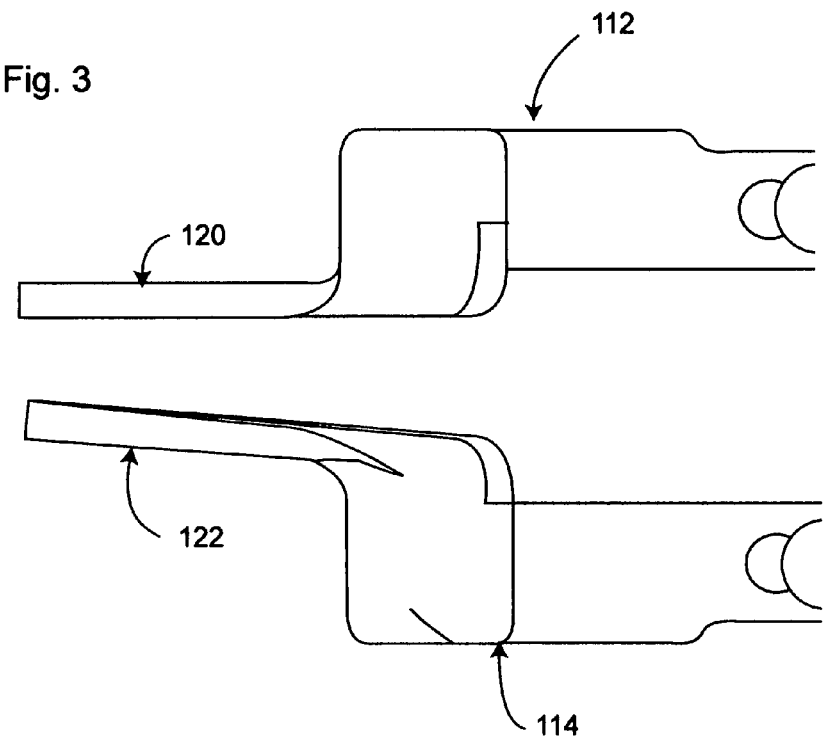
FIG. 3 provides a side view of the upper and lower jaws of the distractor.

FIG. 3 shows a side view of the jaws (112, 114), in which the upper fork tines (120) and lower fork tines (122) are angled relative to each other to approximate a natural lordotic angle between adjacent vertebral bodies.

In this depiction, the upper jaw (112) may be fixed to the distractor assembly (110 in FIG. 2) and the lower jaw (114) may be movable or removable. In this way, a user may select any one of a number of removable lower jaws (114) that correspond to different lordotic angles and attach them to the distractor assembly (116) to accommodate different lordotic angles.

The manner in which the lower jaw (114) is attached to the distractor (110) is a matter for the designer, but may include such attachments as rounded spring-biased pins on the lower jaw locking into indents in the distractor or screws mounting into the distractor body. Of course, the upper jaw (112) may be removable and the lower jaw (114) fixed to the distractor assembly, or both jaws (112, 114) may be removable.

The angled jaws (112, 114) may be selected to accommodate different lordotic angles in the range of 0° to about 25°, perhaps in the range of 0° to about 15°. Utilizing removable jaws having different angles serves multiple purposes. First, by inserting different angled lower jaws, the surgeon will be able to compare the different jaw angles to the lordosis of the vertebral bodies and choose a prosthetic disc having the correct angle between the upper and lower end plates. Secondly, distracting the vertebral bodies at the lordotic angle applies distributed pressure on the vertebral end plates thereby minimizing the potential for damage to those bone surfaces due to uneven distraction forces.

Figure 4:
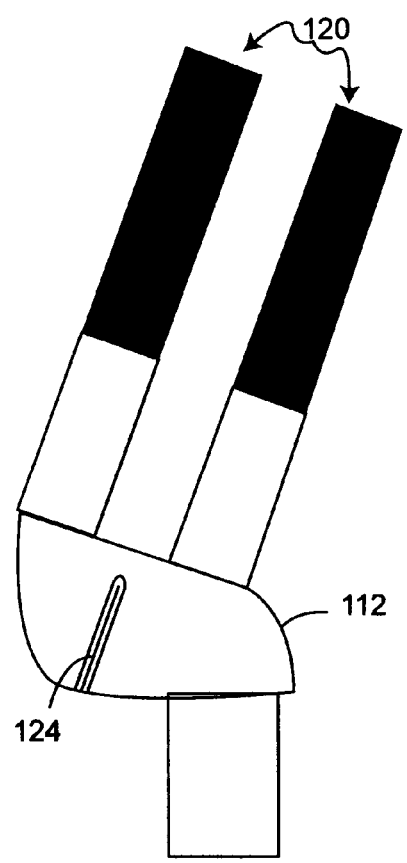
FIG. 4 provides a top view of the upper jaw with offset forks.
Figure 5:
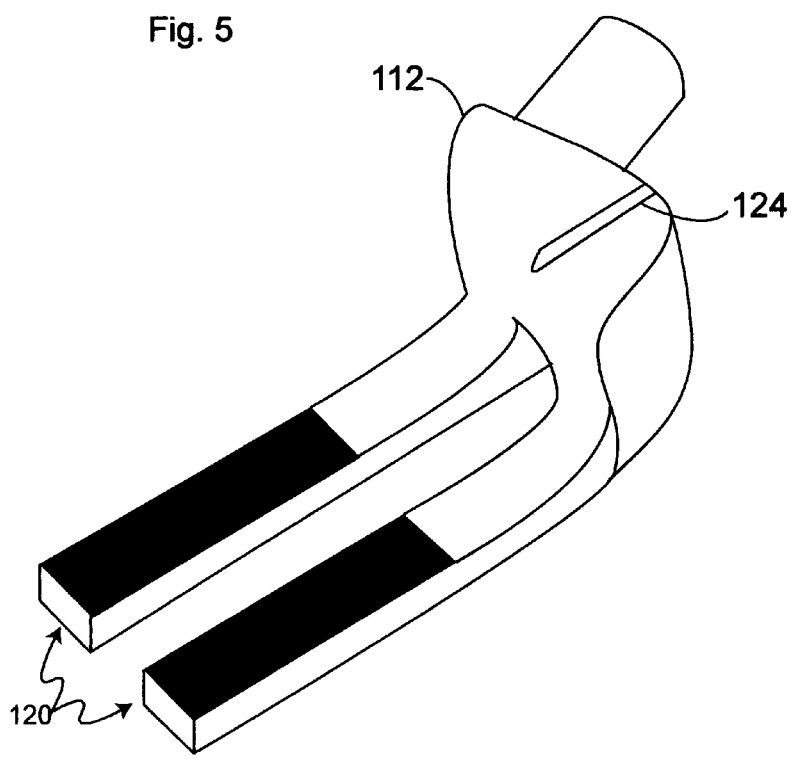
FIG. 5 provides a perspective view of the upper jaw of the distractor.
Figure 6:
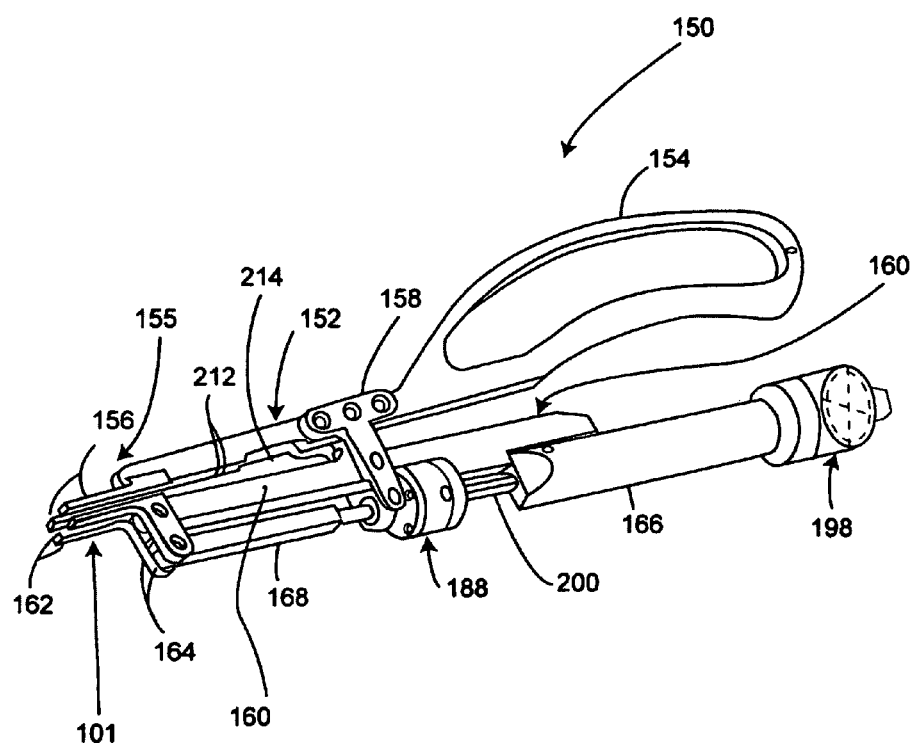
FIGS. 6 and 7 provide perspective views of an adjustable measuring distractor.
Figure 7:
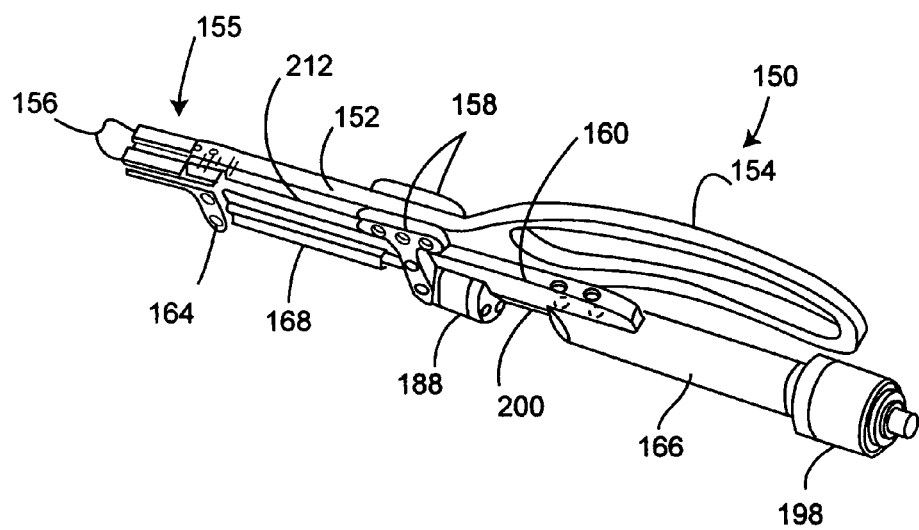
Figure 8:
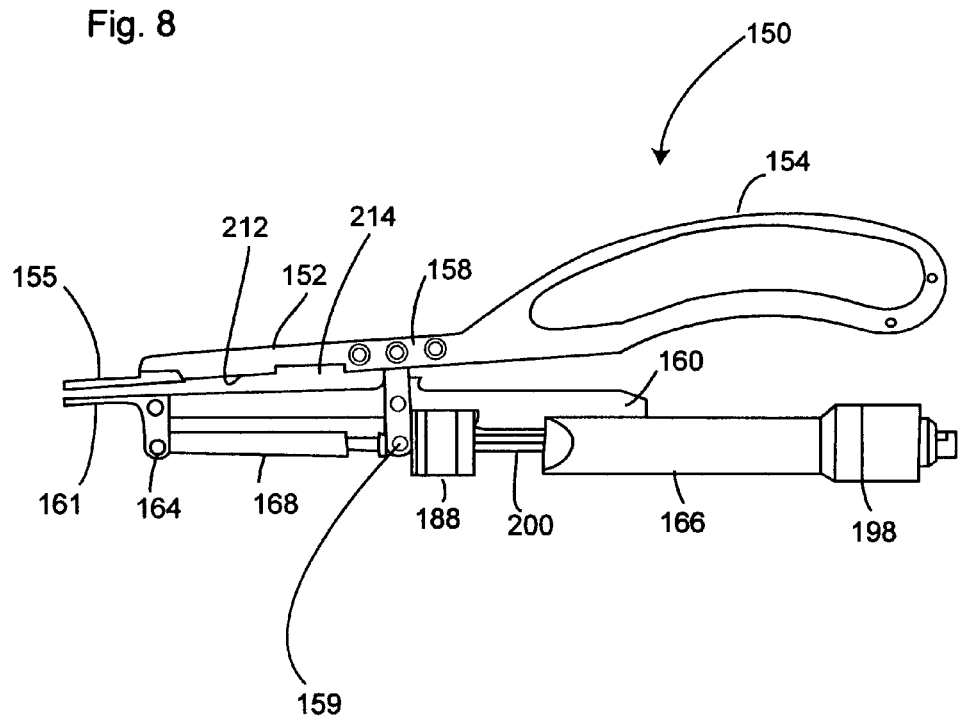
FIG. 8 provides a side view of the adjustable measuring distractor.

FIG. 4 shows a top view and FIG. 5 shows a perspective view of the upper jaw (112), in which the upper jaw (112) and the unseen lower jaw (114) are offset from the longitudinal center axis of the distractor assembly by an angle, e.g., of 200. The centerline (124) of the fork tines (120) is also seen. The angled offset provides a surgeon with a better view of the disc space by angling the distractor assembly out of the way during use. The angled offset also provides easier access to the disc space for inserting trials into the disc space, as explained below. The angled offset may range from 0° to about 90°, perhaps from 0° to about 30° degrees.

FIGS. 6-10 show an adjustable measuring distractor (150) that both distracts adjacent vertebral bodies to create a disc space and also measures the height and lordotic angle of the disc space.

The distractor (150) includes upper lever (152) with an integrated handle (154), distractor fork tines (156) fixed to one end of the upper lever (152), and a pair of T-shaped opposing bars (158) attached to opposite sides of the upper lever and extending downward from the upper lever (152). The distractor (150) also includes a lower lever (160) pivotally connected between the two bars (158) allowing the lower lever (160) to pivot relative to the upper lever (152). The distractor (150) further includes adjustable distractor fork (161) having tines (162). The adjustable distractor fork (161) is pivotally connected to one end of the lower lever (160), and a lower handle (166) attached to the other end of the lower lever (160). The distractor (150) further includes projecting members (164) extending downward from the adjustable fork (161).

The distractor (150) may include a rod (168) pivotally connected at one end between the downward projecting members (164) of the adjustable forks (161) such that translation of rod (168) causes a change in the angle between forks (161) relative to fork tines (156). Movement of the rod (168) away from the forks increases the angle between the fixed and adjustable forks (155, 161); movement of rod (168) toward the forks decreases that angle.

The depicted distractor (150) further includes a rotatable knob (198) on the lower handle (166) that is connected to a rotatable housing nut (188) by a connecting rod (200) such that turning the knob (198) causes the housing nut (188) to rotate.

Figure 10A:
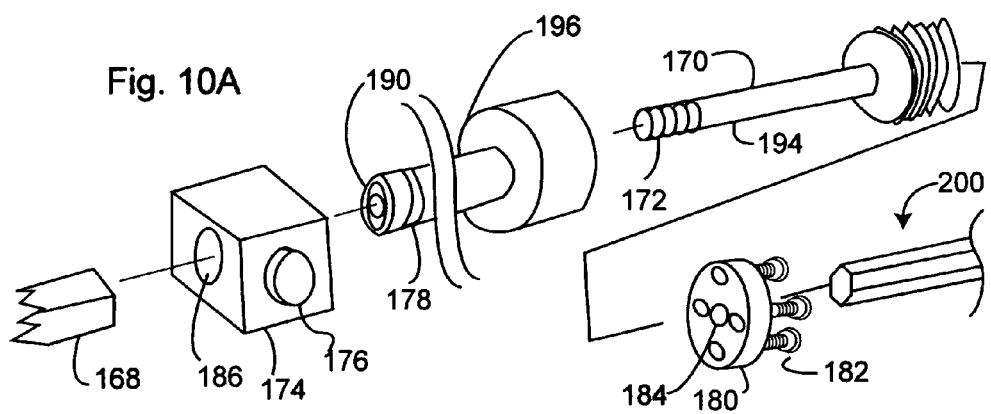
FIG. 10A is an exploded view of the front end of the adjustable measuring distractor.
Figure 10B:
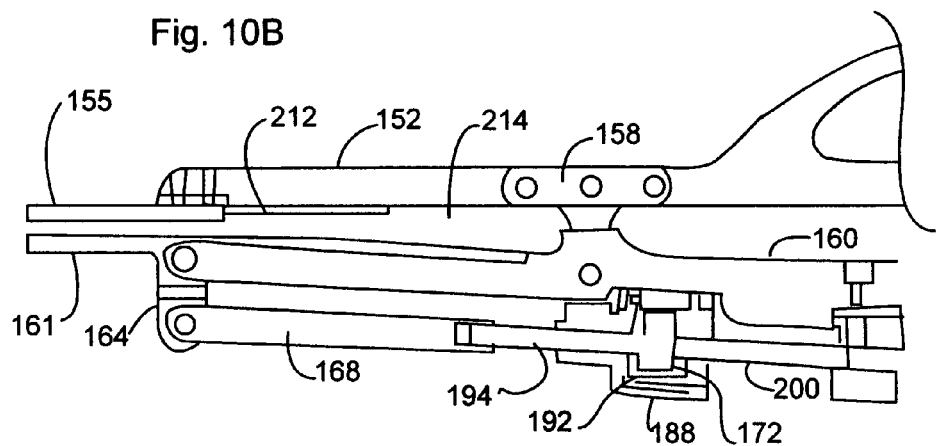
FIG. 10B provides a cross-sectional view of the front end of the adjustable measuring distractor.

FIG. 10A is an exploded view of the mechanism for adjusting the angle of the adjustable distractor forks (162). The mechanism includes the housing nut (188), a shaft (170), back plate (180) for the housing nut (188), and a rectangular mounting member (174). The shaft (170) includes a lead screw portion (172) and an elongated member (194) extending from the lead screw portion (172). The elongated member (194) is inserted through a bore (190) in the housing nut (188) and extends from the housing nut (188). The end of the elongated member (194) is connected to the rod (168) such that the shaft (170) remains rotationally stationary about the longitudinal axis. The lead screw portion (172) of the shaft (170) fits inside an internal compartment (192) of the housing nut (188). The internal compartment (192) includes internal threads (not shown) that engage the lead screw portion (172) of the shaft (170). As a result, rotation of the housing nut (188) about the lead screw portion (172) of the shaft (170) causes the shaft (170) to move relative to the housing nut (188), as explained further below. The back plate (180) is bolted to the back of the housing nut (188) by bolts (182) and includes a hole (184) into which the end of the connecting rod (200) is inserted. In this variation, the hole (184) and connecting rod (200) both have hexagonal cross-sections such that rotation of the connecting rod (200) rotates the housing nut (188). Other shapes may also be used.

The rectangular member (174 shown in FIG. 10A) is pivotally connected in the bottom of the "T" in the "T"-shaped bar (158 in FIG. 8) by inserting projections (176) into openings (159) in the bars (158). The housing nut (188) includes a projecting member (196) that is inserted through a bore (186) in the rectangular member (174). The projecting member (196) includes an annular groove (178) that engages a snap ring (not shown) in the bore (186). This allows the housing nut (188) to rotate relative to the rectangular member (174) but not to translate relative to the rectangular member (174).

In operation, the angle of the adjustable fork (161) relative to the fixed fork (155) is adjusted by rotating or turning knob (198), which rotates the connecting rod (200). The rotation of the connecting rod (200) causes the housing nut (188) to rotate about the screw lead portion (172) of the shaft (192), which remains rotationally stationary about the longitudinal axis. This causes the lead screw portion (172) of the shaft (170) to translate within the internal compartment (192) of the housing nut (188). This in turn causes the elongated member (194) of the shaft (170) and the rod (168) connected to the elongated member (194) to move relative to the rectangular member (174). This translation of the rod (168) changes the angle of the adjustable fork (161) relative to the fixed fork (155). Therefore, rotation of the knob (198) changes the angle of the adjustable fork (161).

Figure 11:
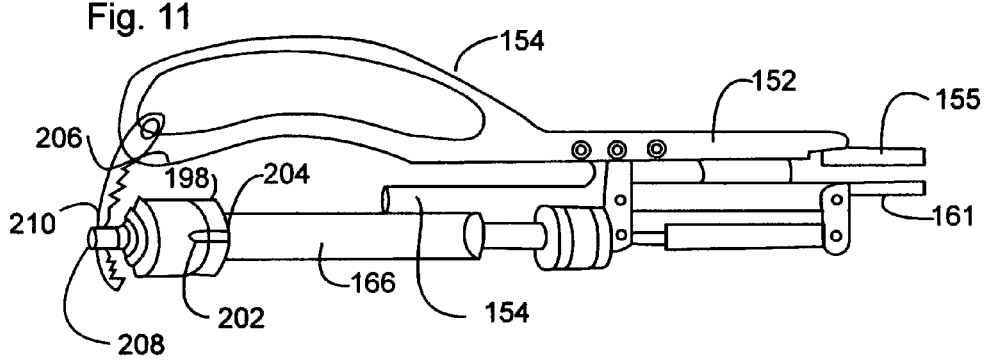
FIG. 11 provides a side view of the adjustable measuring distractor with a latch for measuring an opening height of the forks.

To measure the angle between the fixed and adjustable forks (155, 161), the distractor may include a mark (202) on the knob (198) and angle indicators (204) on the lower handle (166), an example of which is shown in FIG. 11. The angle indicators (204) are arranged on the lower handle (166) so that the mark (202) on the knob (198) lines up with the angle indicator (204) corresponding to the angle between the fixed and adjustable forks (155, 161). Therefore, as the knob (198) is turned to adjust the angle between the forks (155, 161), the mark (202) on the knob (198) lines up with the indicator (204) showing the existing angle between the forks (155, 161).

To adjust the opening between the forks (155, 161), the upper handle (154), and lower handle (160) are moved relative to each other. Squeezing the handles (154) and (160) together increases the opening between the forks (155, 161) by moving the ends of the upper and lower levers (152) and (160) apart. To measure the opening between the forks (155, 161), a latch (206) may be connected to the upper handle (154), an example of which is shown in FIG. 1. The lower handle (166) includes a projection (208) extending from its proximal end. The projection (208) includes a slot (210) and the latch (206) slides through the slot (210). The position of the projection (208) on the latch (206) changes as the opening between the forks (155, 161) changes. Therefore, the position of the projection (208) on the latch (206) can be used to measure the height of the opening between the forks (155, 161). The latch (206) may include height indicators arranged on the latch (206) such that the projection (208) lines up with the height indicator corresponding to the height of the opening between the forks (155, 161). The latch (206) may also be used to lock the forks (155, 161) at a desired opening height.

Figure 12:
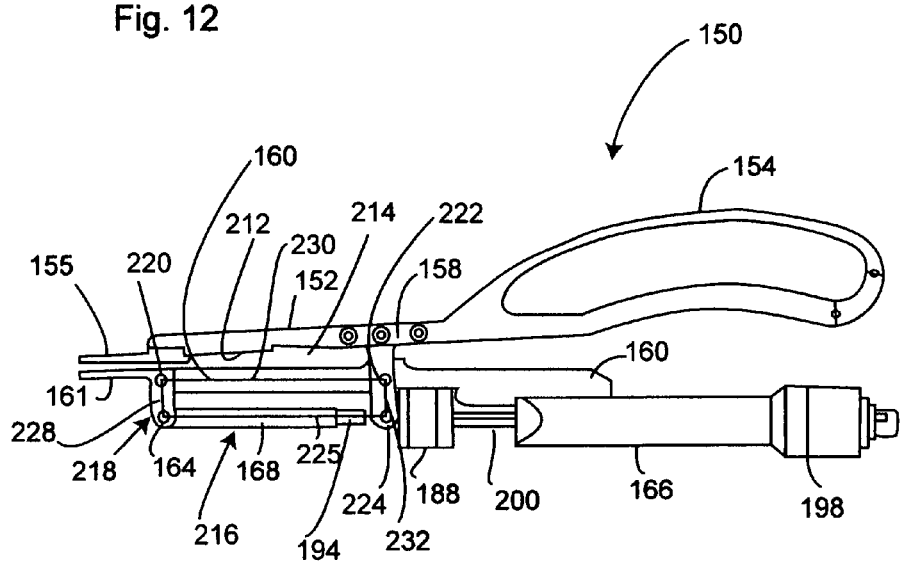
FIG. 12 shows a four-bar linkage formed by the adjustable measuring distractor.

FIG. 12 shows a practical mechanism for adjusting both the angle of the jaws and their separation. The distractor variation shown in the drawing forms a four-bar linkage (216). The four-bar linkage (216) includes two links (226, 230) connected to two other links (228, 232) by pivots (218, 220, 222, 224) to form a closed loop. Link (226) is formed by the rod (168) and the portion of the elongated member (194) connected between pivot (218) and pivot (224). Link (228) is formed by the portions of the downward extending members of the adjustable fork (161) between pivot (218) and pivot (220). Link (230) is formed by the portion of the lower lever (160) connected between pivot (220) and pivot (222). Link (232) is formed by the portions of the bars (158) between pivot (222) and pivot (224). Fixed fork (155) is rigidly connected to link (232) through the bars (158) and upper lever (152).

The length of link (226) is adjusted by rotating or turning knob (198). Rotating the knob (198) moves the elongated member (194) axially relative to rectangular member (174) and pivot (224), which in turn changes the length of the portion of the elongated member (194) forming link (226). This adjustment in the length of link (226) in turn changes the angle of adjustable fork (161).

In this four-bar linkage (216), movements of the upper and lower levers (152, 160) relative to each other, adjust the distance between the forks (155, 161) but do not affect the relative angle between the fixed and adjustable forks (155, 161). The relative angle between the forks (155, 161) is adjusted by changing the length of link (226) by rotating or turning the knob (198). The position of the mark on the knob (198) then reflects the relative angle between the adjusting forks (161) and the fixed forks (155) independent of the opening height.

The distractor (150) further includes tracks (212) for aligning the upper recesses of a trial with the fixed forks (155) of the distractor (150). The tracks (212) are dimensioned to fit into the upper recesses of the trial to be implanted and are aligned with the fixed forks (155). The tracks (212) serve as a guide that aligns the recesses of the trial with the distractor forks (155, 161). A space (214) large enough to accommodate loading the trial is provided.

Turning to FIGS. 13-19, and FIG. 23, the implantation tools or tool set includes a number of different sized trials corresponding to different heights and/or lordotic angles between adjacent vertebral bodies. As explained below, a progression of different sized trials may be inserted into the disc space to determine the proper size and position of the prosthetic disc to be implanted. But, for clarity of explanation, only one trial (252) is shown in FIGS. 13-19, and FIG. 23.

Figure 13:
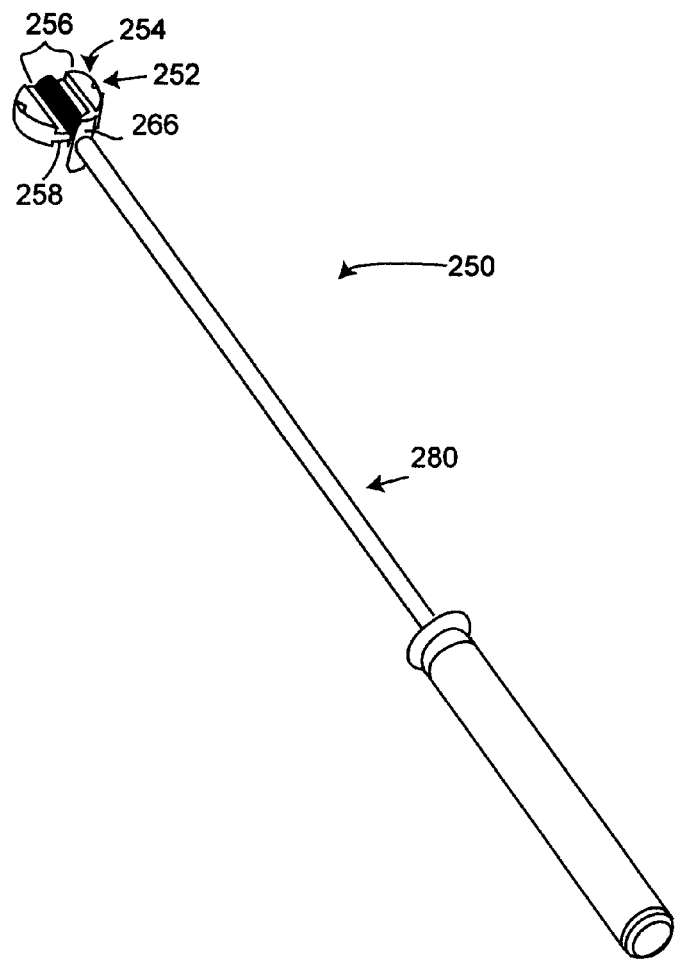
FIG. 13 provides a perspective view of a trial assembly showing the trial attached to a quick release handle.

FIG. 13 provides a perspective view of a trial assembly (250) including the trial (252), a disc portion (254), a stop (266) for limiting the depth of penetration of the trial (252) into a disc space, and grooves (256) for receiving the distractor described just above. Also shown is the handle (280) that may be of a quick-release design.

Figure 14:
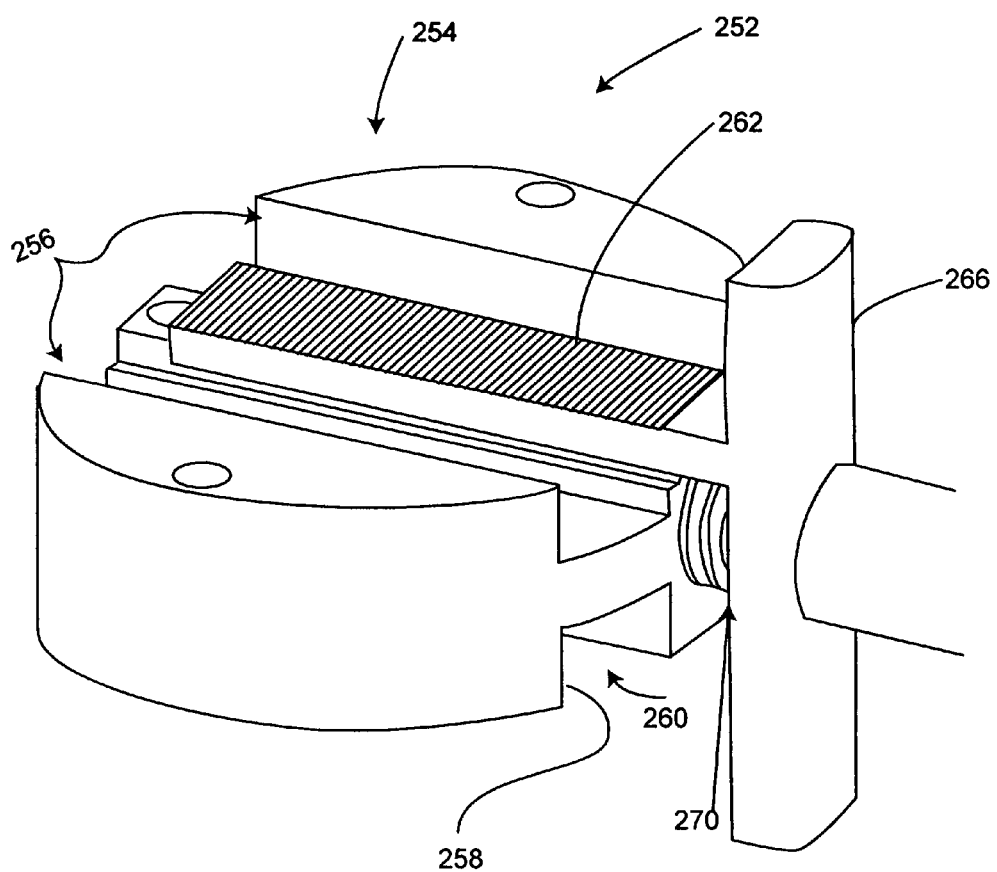
FIG. 14 provides a perspective view of a trial with an adjustable stop.

As may be seen in FIG. 14, each trial (252) includes a disc portion (254) having two upper recesses (256) on an upper surface and two lower recesses (258) on a lower surface (260). The disc portion (254) is dimensioned to correspond to a prosthetic disc of a particular size and lordotic shape. The recesses (256, 258) are arranged and dimensioned so that the distractor fork tines (120, 122) fit in the recesses (256, 258) of the disc portion (254). As explained below, this arrangement allows the trial (252) to be inserted in the disc space between fork tines (120, 122). The recesses (256, 258) may, of course, have other configurations and dimensions depending on the form of the chosen distractor forks.

Also as is seen in FIG. 14, this variation of the trial (252) further includes a foot (262) that slideably engages the disc portion (254) and an adjustable stop (266) shown to be fixedly connected to foot (262). The adjustable stop (266) is adjustably connected to the disc portion (254) by a lead screw (270) that allows controlled movement of the adjustable stop (266) relative to the disc portion (254).

Figure 15:
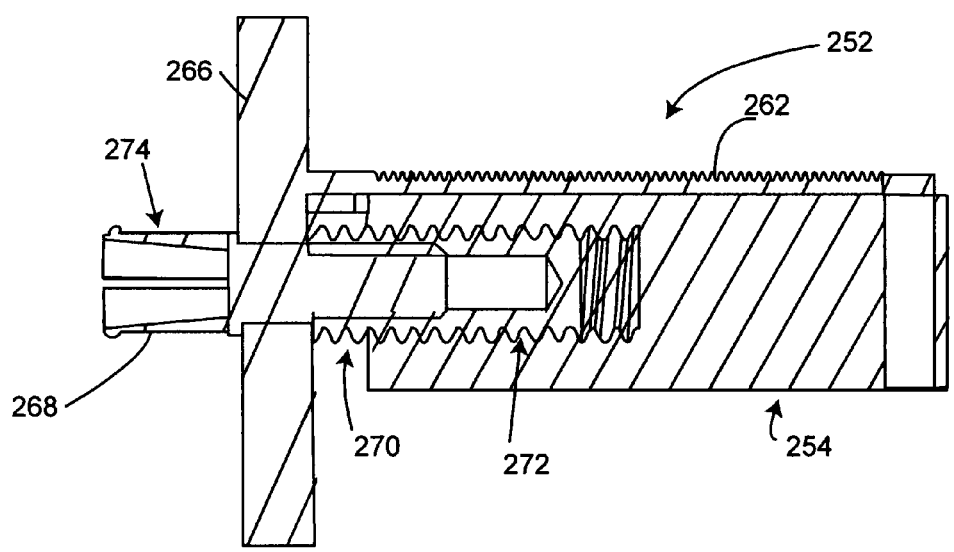
FIG. 15 provides a cross-sectional view of the trial.

FIG. 15 shows a cross-sectional side view of the trial (252) illustrating the operation of the lead screw (270). The lead screw (270) is helically grooved and engages corresponding grooves (272) in the disc portion (254). The lead screw (270) passes through the adjustable stop (266) and is connected at its proximal end (268) to a quick release handle (280) (shown in FIG. 13) via a crenellated stud (274). The lead screw (270) may be sized by choice of screw pitch so that a specific rotational movement of the handle (280) moves the adjustable stop (266) a specific distance. For instance, the pitch of the lead screw (270) may be selected so that a 1800 turn of lead screw (270) moves the adjustable stop (266) about 1 mm relative to the disc portion (254). The total range of motion of the adjustable stop (266) relative to the disc portion (254) generally may be between about 1 mm and 10 mm, perhaps between about 1 mm to 5 mm, and between 1 mm and 3 mm.

Figure 16:
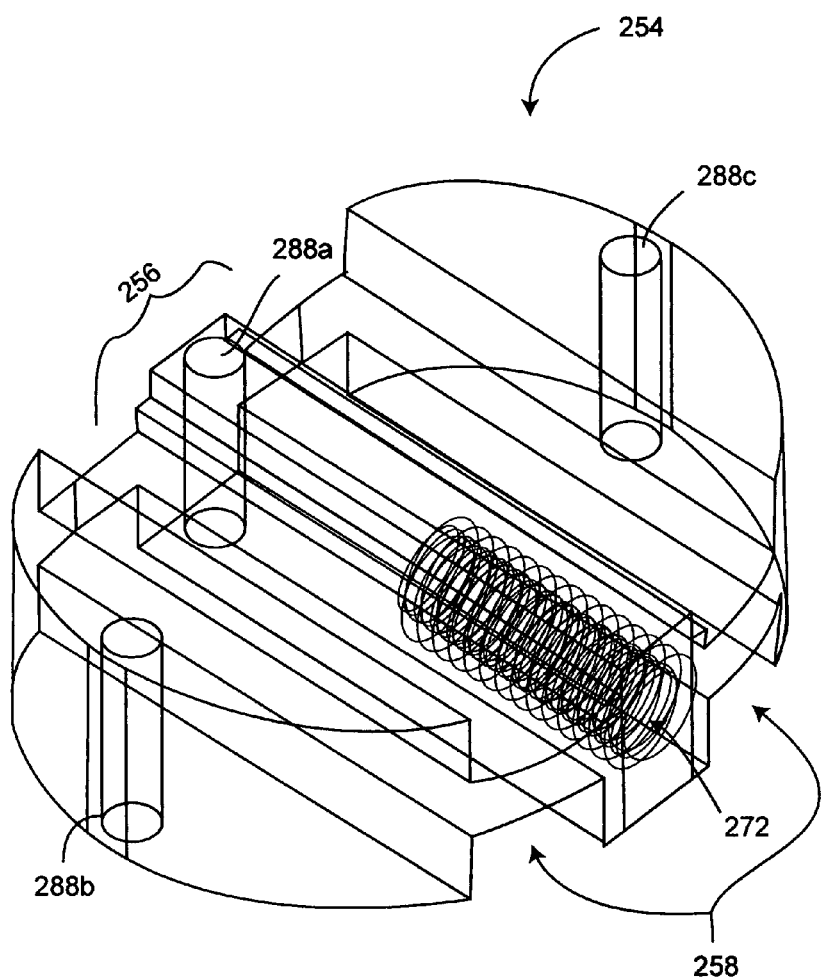
FIG. 16 provides a perspective ghost view of the trial showing radio-opaque pins in the trial.

FIG. 16 shows a perspective line drawing of disc portion (254) in a "ghost" format. This drawing shows optional radio-opaque pins (288a, 288b, 288c) placed in the distal nose and in the lateral edges of the disc portion (254). These pins (288a, 288b, 288c) allow visualization of the trial's position (e.g., lateral position and anterior-posterior (AP) depth) in the disc space. As an alternative, the disc portion (254) may be radio-opaque and include radio-visible openings allowing for similar ease of trial positioning under fluoroscopy.

Figure 17:
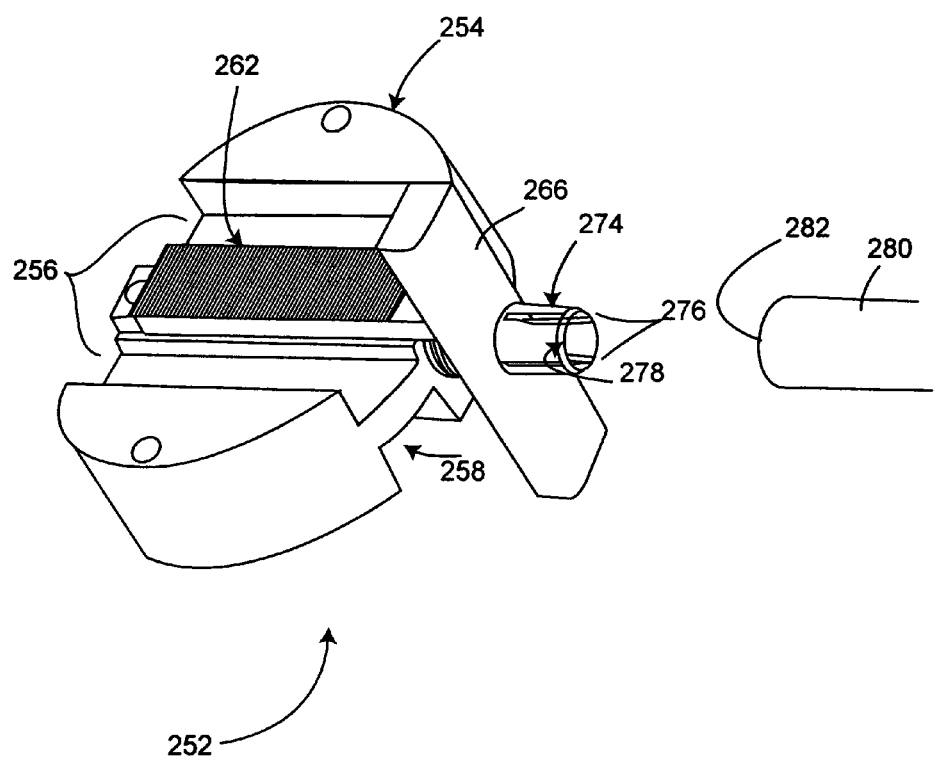
FIGS. 17 and 18 provide two perspective views of the trial with a crenellated stud that is inserted into an opening in the quick release handle to attach the trial to the handle.
Figure 18:
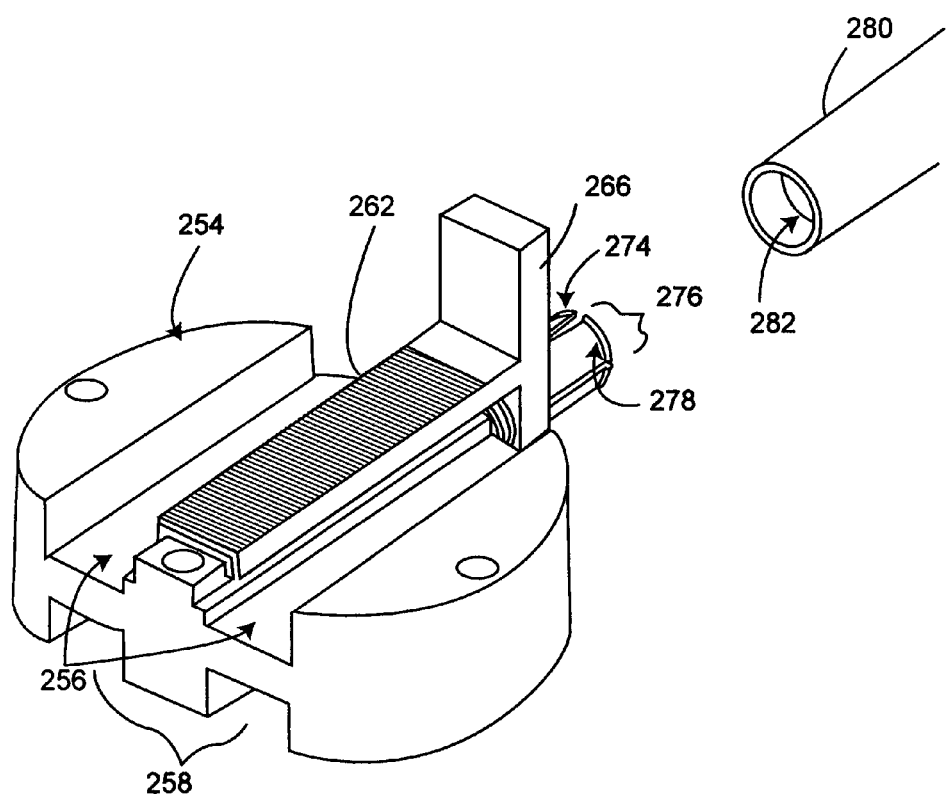
Figure 19:
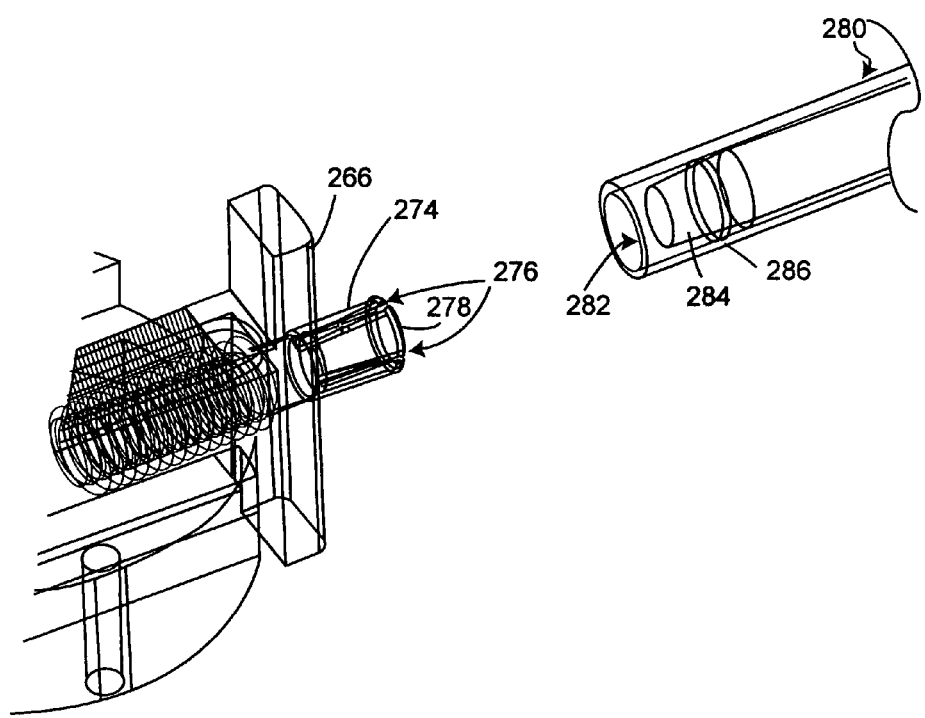
FIG. 19 provides a perspective ghost view of the trial and the quick release handle.

As is shown in FIGS. 17-19, the trial (252) may further include an attachment point such as the illustrated crenellated stud (274) for attaching the trial (252) to the quick release handle (280). The crenellated stud (274) has a generally cylindrical shape with long narrow slits (276) axially around its perimeter, which allow the diameter of stud (274) to expand when the interior of the stud (274) is penetrated by a cooperating extension (284 in FIG. 19) within the end handle (280). The stud (274) also includes a small circumferential flange (278) at its proximal end. To attach the trial (252) to the handle (280), the crenellated stud (274) is inserted into an opening (282) at the distal end of the handle (280).

Turning to FIG. 19, as the stud (274) is inserted into the opening (282), a conical cooperative extension (284) engages the inner surface of the stud (274) causing the diameter of stud (274) to expand. The conical cooperative extension (284) extends to the proximal end of the handle (280) and may be moved axially within the handle. This expansion causes the flange (278) at the proximal end of the stud (274) to enter an inner annular slot (286) within the handle (280), thereby locking the trial (252) to the handle (280). The trial (252) is released from the handle (280) by retracting the conical cooperative extension rod (284). This retraction allows the diameter of stud (274) to return to its unexpanded shape and the flanges (278) to disengage from the inner annular ring (286). The trial (252) and the handle (280) may then be pulled apart. The conical cooperative extension rod (284) has, in this variation, the additional function of participating in the movement of the lead screw assembly described with respect to FIG. 15. Consequently, the handle (280) and the conical cooperative extension rod (284) may move in concert in twisting the lead screw (270) to adjust stop (266). Those skilled in the art will appreciate that other release mechanisms may be used. Such alternative release mechanism should permit the step of twisting the lead screw (270) to adjust the stop (266), however.

Figures 20A, 20B:
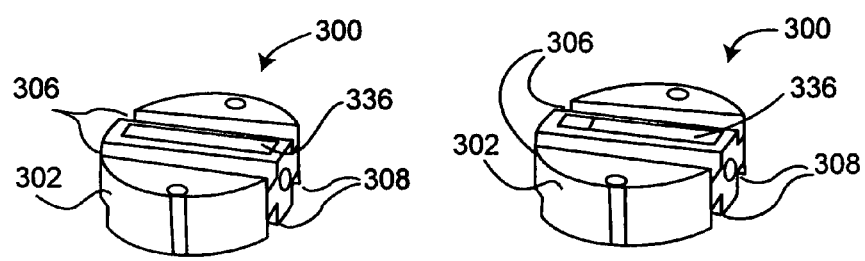
FIG. 20A provides a perspective view of a trial with a retractable foot in a raised position.
FIG. 20B provides a perspective view of the trial with the retractable foot in a recessed position.

FIGS. 20A and 20B show a trial (300) having a retractable foot (336) that can be raised from and retracted into the disc portion (302) of the trial (300). The trial (300) may have retractable feet both on the upper surface of the disc portion on the lower surface. Only the upper foot (336) is shown in FIGS. 20A and 20B. FIG. 20A shows the foot (336) raised from the disc portion (302) of the trial and FIG. 20B shows the foot (336) retracted into a recess (340) in the disc portion (302) of the trial. These upper foot positions are better shown in FIGS. 21A and 21B discussed below. The outer surface of the foot (336) may be roughened by adding ridges (or the like) to the contact surface to provide increased traction with the vertebral bodies. Other types of surfaces to increase traction, e.g., grooving, knurling, adding bumps, or lumps, are also suitable.

Figure 21B:
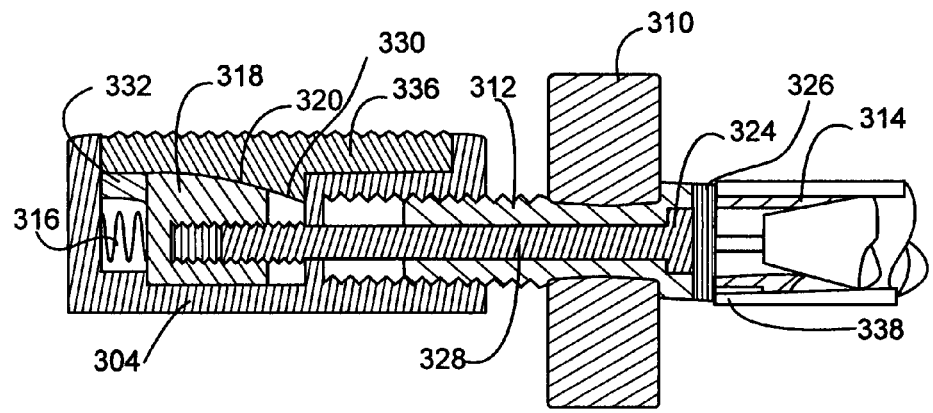
FIG. 21B provides a cross-sectional side view of the mechanism in FIG. 21A, in which the trial is attached to a handle and the retractable foot is shown in a retracted position.
Figure 21A:
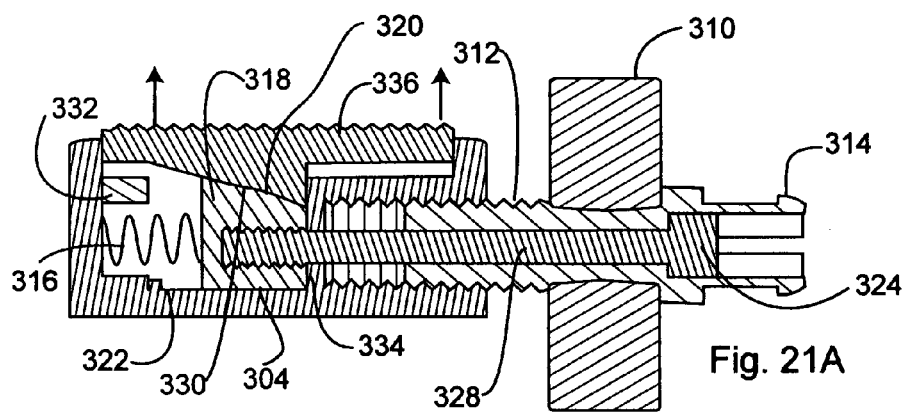
FIG. 21A provides a cross-sectional side view of a mechanism for raising and lowering a retractable foot in a trial. The retractable foot is shown in the raised position.

Trial (300) also includes upper recesses (306) and lower recesses (308) for cooperatively receiving distractor fork tines (120, 122) and chisel heads (350, 362), and an adjustable stop (310) and lead screw (312) (shown in FIGS. 21A and 21B).

Trial (300) is especially practical because the foot (336) may be retracted into trial (300) to lower the overall thickness of the trial during the step of inserting the trial (300) into the disc space. After the trial (300) is positioned in the disc space, the foot (336) may be extended to engage the vertebrae and secure the trial in place. Securing the trial between the vertebral bodies is more important when the lordotic angle between the vertebral bodies is high because of the tendency of the trial to move forward (toward the anterior). Prior to removing the trial (300) from the disc space, the foot (336) is retracted back into the trial.

The trial may have two or more two retractable feet. For example, the trial may have a retractable foot on each of its upper and lower surfaces for engaging both vertebral bodies.

FIGS. 21A and 21B show an example of a retracting mechanism for raising and lowering such a retractable foot (336). The mechanism includes a wedge block (318) that is slideable within an inner compartment (322) of the trial body (304) and is biased by a spring (316). The retractable foot (336) has a sloped bottom surface (320) that interfaces with a sloped upper surface (330) of the wedge block (318) such that the foot (336) moves up or down as the wedge block (318) slides within the compartment (322).

The retracting mechanism further includes a retractor rod (328) running through the lead screw (312). The retractor rod (328) can slide within the lead screw (312), and is connected at one end to the wedge block (318) and has an engagement head (324) at the other end. The engagement head (324) is located within the crenellated stud (314) similar to the one shown in FIG. 18.

FIG. 21A shows the retracting mechanism in an extended configuration when the release handle is not connected to the trial. In this configuration, the spring (316) biases the wedge block (318) against inner surface (334), which raises the foot (336) to the raised or extended position. In addition, the engagement head (324) is pushed out within the crenellated stud (314). Thus, when the release handle is not connected to the trial, the foot (336) is in the raised or extended position.

Figure 22:
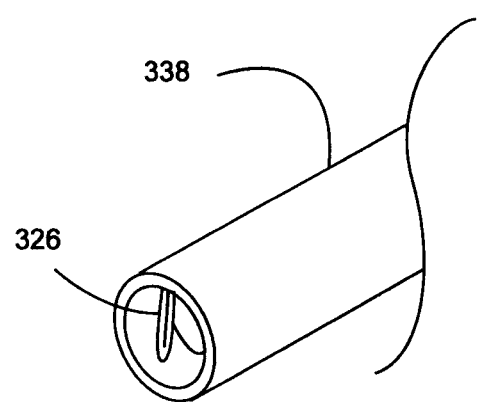
FIG. 22 provides a perspective view of a handle with a cross bar in the opening of the handle.

FIG. 21B shows the retracting mechanism in a lowered or recessed configuration when the release handle (326) is connected to the crenellated stud (314). The opening of the handle (338) includes a cross bar (326) that slides through the slots in the crenellated stud (314), similar to the slots (276) shown in FIG. 17. FIG. 22 shows a perspective view of the cross bar (326) in the opening of the handle (338). When the release handle (326) is connected to the crenellated stud (314), the cross bar (326) slides through the slots in the crenellated stud (314) and engages the engagement head (326) of the retracting rod (328), pushing the retractor rod (328) forward against the force of the spring (316). This causes the retractor rod (328) to push the wedge block (318) forward against the force of the spring (316), thereby lowering or retracting the retractable foot (336). A stop (332) limits the amount that the wedge block (318) may be pushed forward. Thus, when the release handle is connected to the trial, the foot (336) is retraced into the trial.

The cross bar (326) also facilitates the transfer of torque from the handle to the crenellated stud (314) to rotate the lead screw (312) and adjust the position of the stop (310). When the cross bar (326) is inserted through the slots in the crenellated stud (314) and applies torque to the crenellated stud (314) when the handle is turned. The cross bar (326) may also be used in the embodiment shown in FIG. 18 for this purpose.

Trial (300) may be used thusly: to insert the trial (300) into the disc space, the foot (336) is retracted into the disc portion (302) of the trial and the disc portion (302) is inserted between the distractor fork tines in the disc space by fitting the fork tines (120, 122) into trial recesses (306, 308). The adjustable stop (310) is butted against the anterior surfaces of the vertebral bodies. The AP depth of the disc portion (302) is then adjusted by turning the lead screw (312) with the quick release handle. After the disc portion (302) is positioned in the disc space, the foot (336) is raised to engage the vertebral bodies and secure the trial between the vertebral bodies. The distractor fork tines (120, 122) are then removed and the chisel heads (350, 362) are inserted into the recesses (306, 308) to cut the grooves in the vertebral bodies. The raised foot (336) prevents trial (300) from moving during the chiseling steps. Before removing the trial (300) from the disc space, the foot (336) is retracted back into the disc portion (302).

Figure 23:
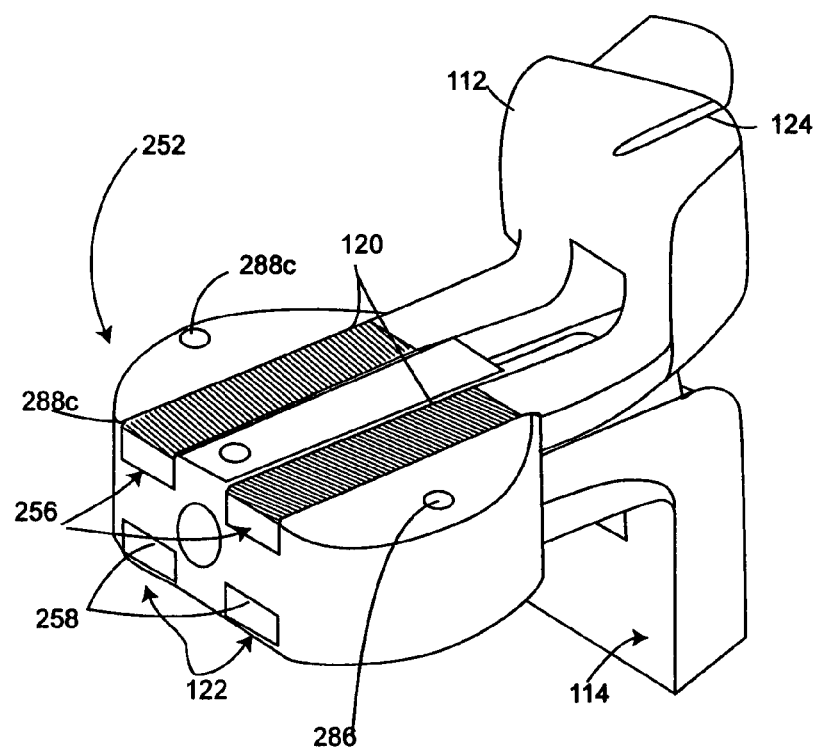
FIG. 23 provides a perspective view of the distractor fork tines inserted into recesses in a trial.

FIG. 23 shows the trial (252) inserted between the distractor fork tines (120, 122) with those fork tines (120, 122) fitting into the trial's upper and lower recesses (256, 258). The distractor fork tines (120, 122) prevent the trial (252) from "over-distracting" the vertebral bodies by bounding the upper and lower surfaces of the trial (252) so that the trial does not further distract the vertebral bodies. Fork tines (120, 122) serve as slidable guides for trial (252) and may also be used to visibly align the center the trial (252) with the centerline of the vertebral bodies. A centerline alignment mark (124) may be seen in the FIG. 23. The ends of optional radio-opaque pins (288a, 288b, and 288c) are seen in the disc section (254) and may be used further to determine the location of the trial (252) relative to the adjacent vertebrae.

Turning to FIGS. 24-27 and FIG. 28A, the tool system for implanting prosthetic discs may include chisels for cutting grooves in the vertebral bodies for fixation of the prosthetic disc to the vertebral bodies.

Figure 24:
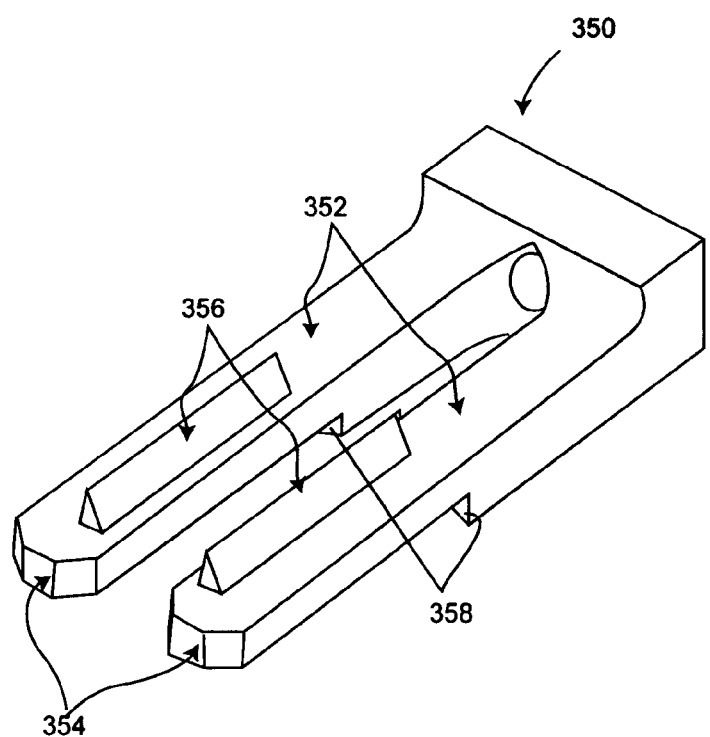
FIG. 24 provides a perspective view of an upper chisel head.

FIG. 24 shows an upper chisel head (350) for cutting grooves in the lower surface of the upper or superior adjacent vertebral body. The depicted upper chisel head (350) includes two arms (352) that are sized to fit into the upper recesses (256) of the trial (252). The leading edges (354) of the arms (352) may have generally trapezoidal shapes to facilitate insertion of the arms (352) into the recesses (256) of the trial (252). The chisel head (350) further includes a pair of blades (356) one on each arm (352) for cutting the grooves. In the depicted variation, each blade (356) has a triangular cross section; however, other blade shapes may be used. The number, shape, and orientation of the blades (356) match the anchor fins of the prosthetic disc to be implanted. The upper chisel head (350) also includes stop flanges (358) that engage a surface on the trial (252) to control the depth to which the chisel arms (352) can be inserted into the trial.

Figure 25:
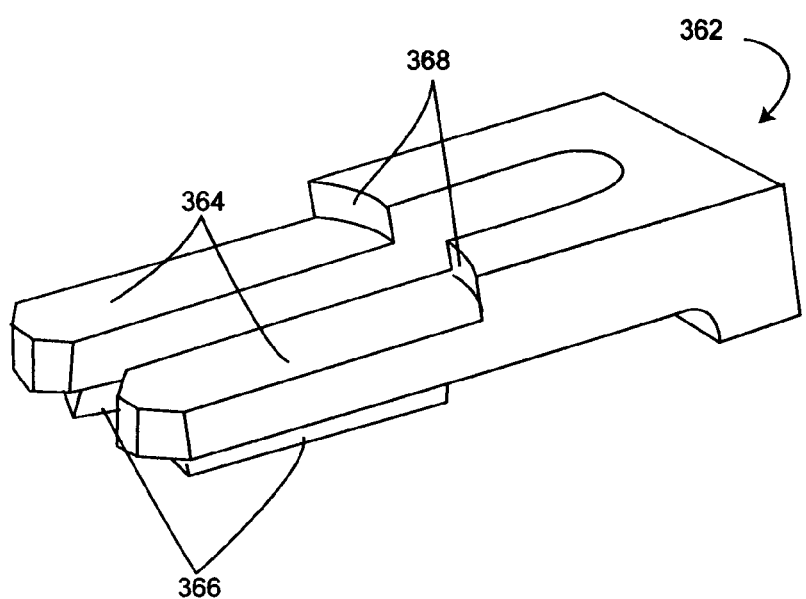
FIG. 25 provides a perspective view of a lower chisel head.

FIG. 25 shows a lower chisel head (362) similar in function and shape to the upper chisel head (350) shown in FIG. 24. The lower chisel head (362) is used to cut grooves in the upper surface of the lower or inferior vertebral body that is to be in contact with the prosthetic disc. The lower chisel head (362) includes two arms (364) that fit into the lower recesses (258) of the trial (252). The lower chisel head (362) further includes a blade (366) on each arm (364) for cutting the grooves. The lower chisel head (362) also includes stop flanges (368) that engage a surface of the trial (252) to control the depth to which the chisel arms (364) may be inserted into the trial (252).

Figure 26A:
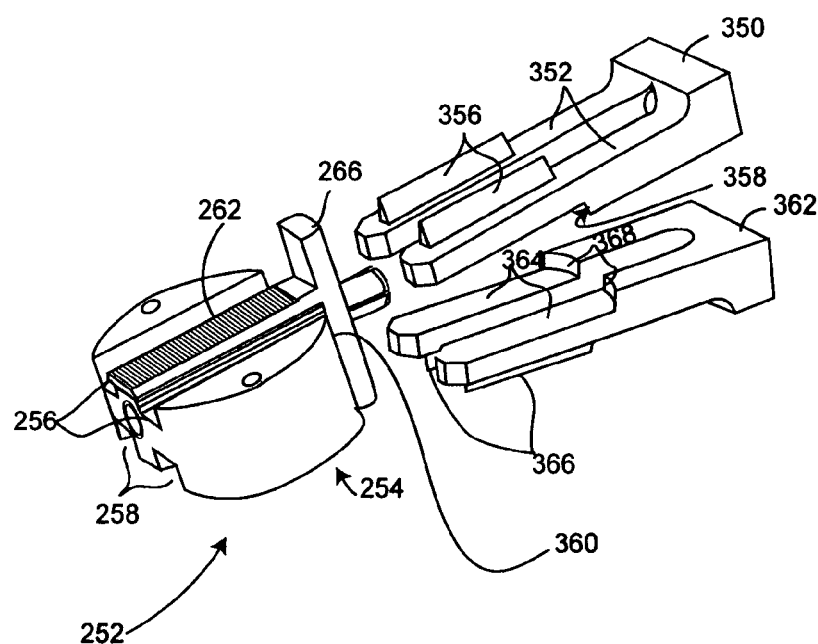
FIG. 26A provides a perspective view of the trial and the two chisel heads.
Figure 26B:
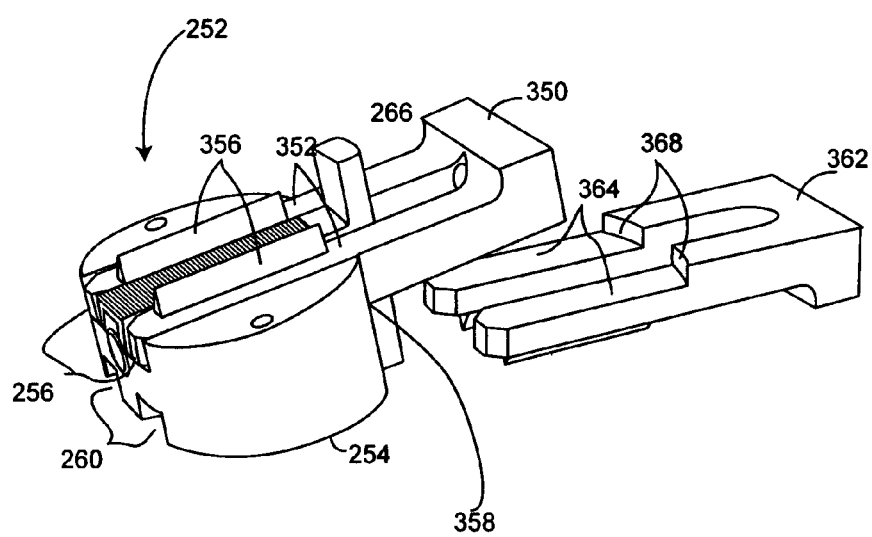
FIG. 26B provides a perspective view of the trial with one of the chisel heads inserted into recesses in a trial.
Figure 26C:
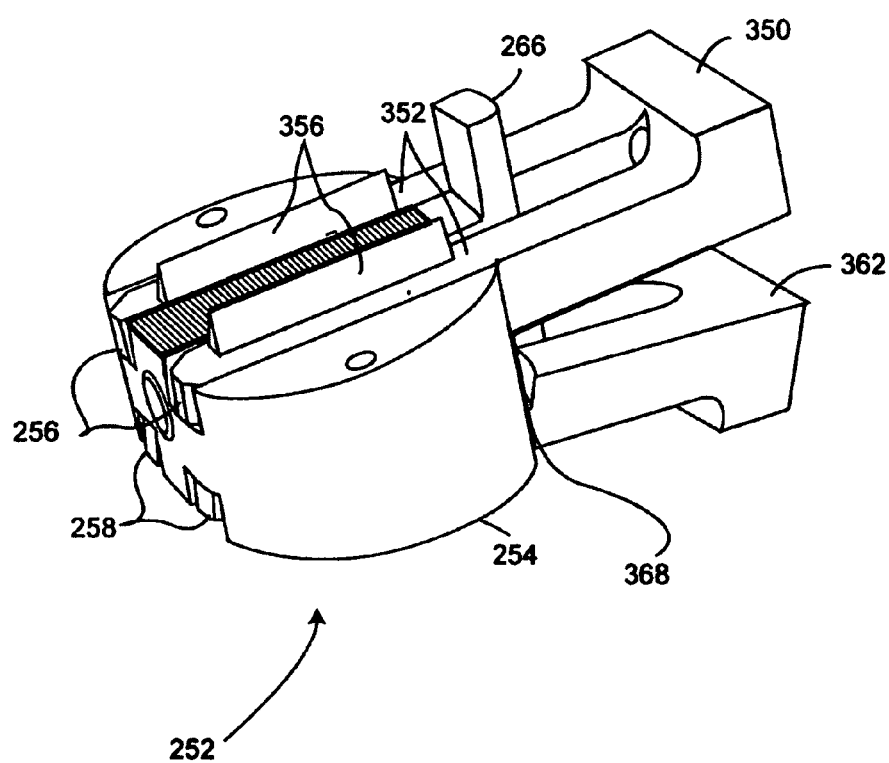
FIG. 26C provides a perspective view of the trial with both chisel heads inserted into recesses in a trial.

FIGS. 26A-26C show the physical relationships amongst the upper chisel head (350), the lower chisel head (362) and the trial (252) as the respective chisel heads (350, 362) are used to cut grooves in the adjacent vertebrae. The procedure of use will be explained in greater detail below.

FIG. 26A shows the upper chisel head (350) with arms (352) as it approaches trial (252) and the trial's cooperating upper grooves (256). The stops (358) on the upper chisel head (350) may be seen and the relationship of the proximal surfaces (360) on the trial (252) to those stops may be appreciated. Similarly, lower chisel head (362) with arms (364) may be seen approaching the trial's cooperating lower grooves (258). Again, the stops (368) on the lower chisel head (362) may be seen.

FIG. 26B is similar to the view shown in FIG. 26A, excepting that the upper chisel head (350) has been inserted into trial (252). The arms (352) of upper chisel head (350) are seated in the cooperating upper grooves (256). The stops (358) on the upper chisel head (350) are against the trial (252).

FIG. 26C is similar to the views shown in FIGS. 26A and 26B, excepting that both the upper chisel head (350) and the lower chisel head (362) have been inserted into trial (252). The stops (368) on the lower chisel head (362) may be seen approaching the trial (252). This view depicts the positions of the upper chisel head (350) and the lower chisel head (362) after the prosthetic disc mounting grooves have been cut into the two adjacent vertebrae.

FIGS. 27A-27E show perspective views of various components used in conjunction with the chisel heads to cut the grooves in the vertebral bodies and to remove the chisel heads from the spinal disc space.

Figure 27A:
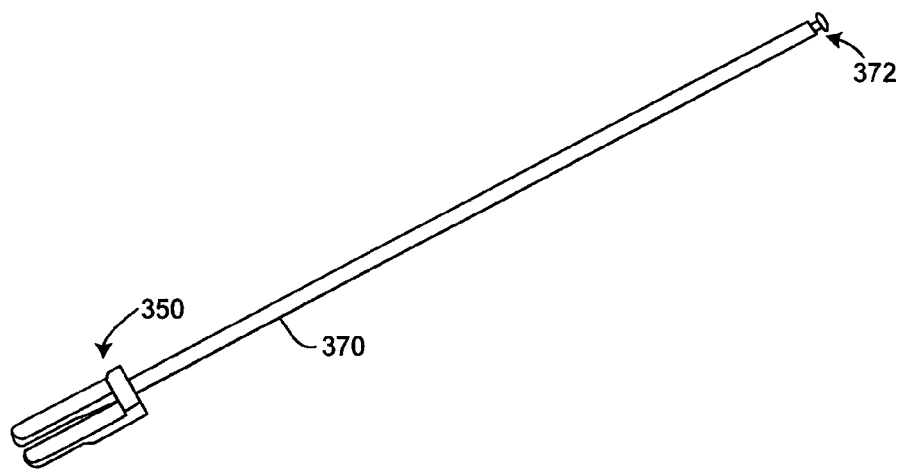
FIG. 27A provides a perspective view of an extended chisel head with a rod extending from the proximal end of the chisel head.
Figure 27B:
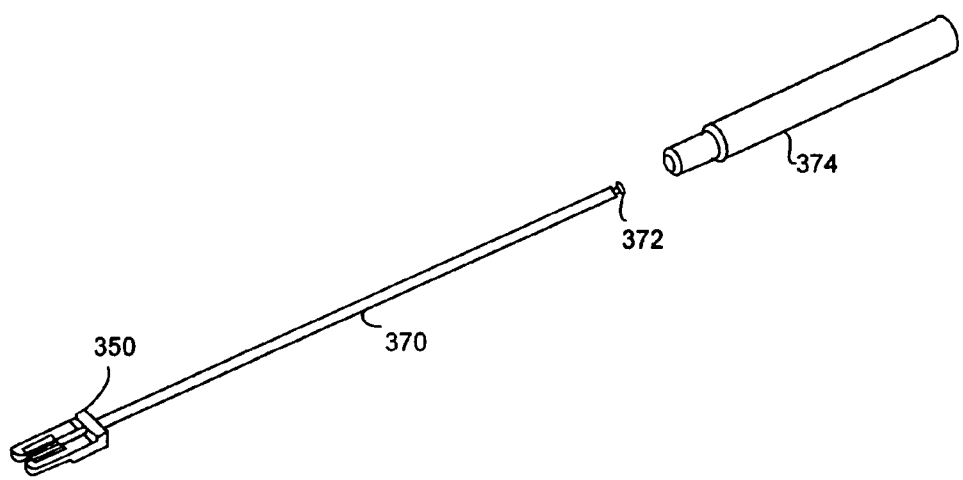
FIG. 27B provides a perspective view of the extended chisel head and a handle.
Figure 27C:
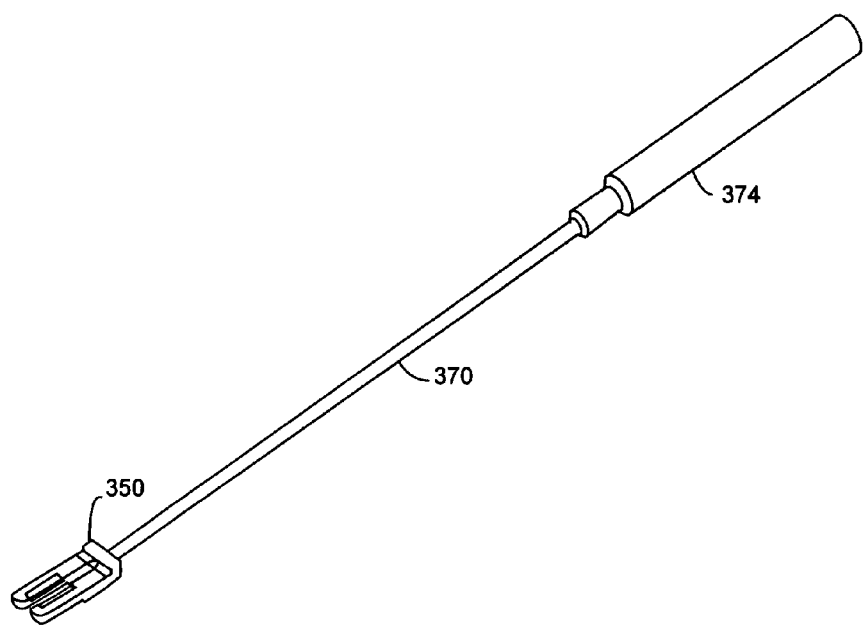
FIG. 27C provides a perspective view of the extended chisel head attached to the handle.

FIG. 27A shows the upper chisel head (350) connected to a rod (370) extending from the proximal end of the chisel head (350). The rod (370) includes an optional quick release feature (372) at its proximal end for attaching a handle (374) to the upper chisel head (350), an example of which is shown unattached in FIG. 27B and attached in FIG. 27C.

Figure 27D:
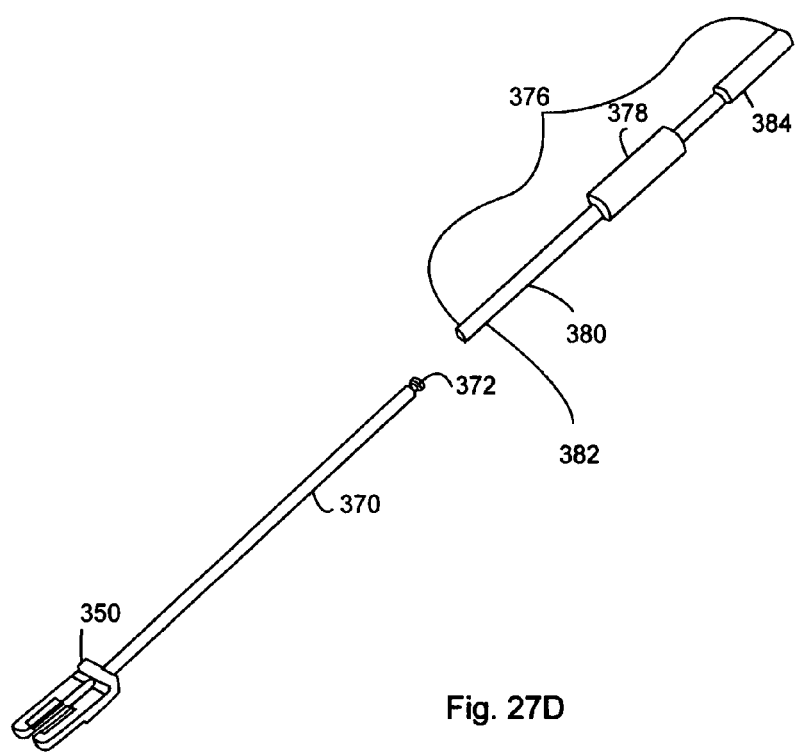
FIG. 27D provides a perspective view of the extended chisel head and a slide hammer.
Figure 27E:
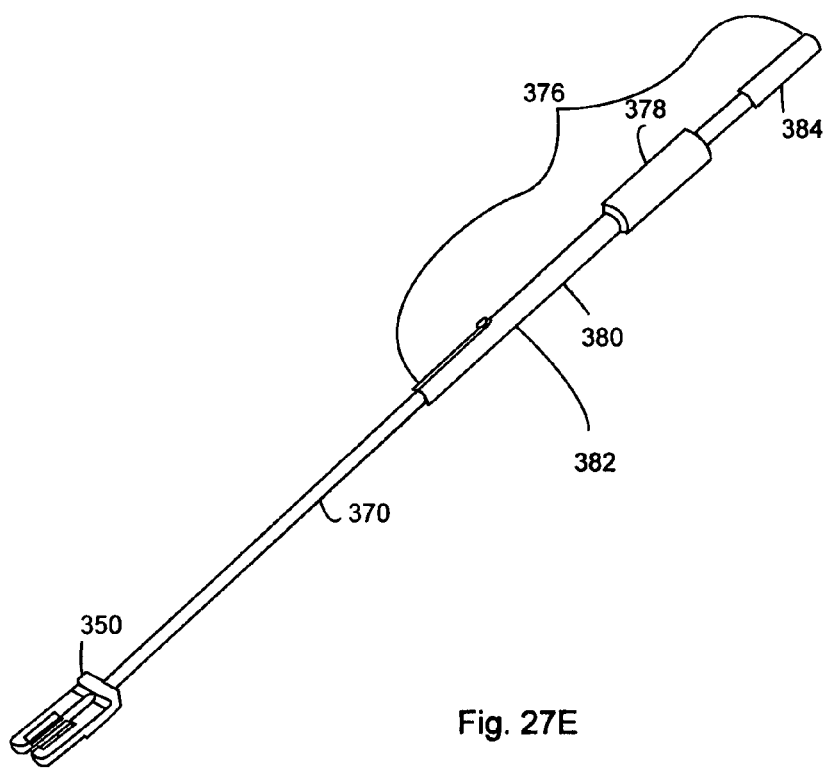
FIG. 27E provides a perspective view of the extended chisel head attached to the slide hammer.

As is shown in FIGS. 27D and 27E, the quick release feature (372) may be used to also allow a slide hammer assembly (376) comprising to a hammer slide (378), a slide shaft (380), a connector (382) allowing connection to rod (370) via quick release feature (372), and a hammer stop (384). The slide hammer assembly (376) is thus attached to the upper chisel head (350) allowing removal of the upper chisel head (350) after the grooves are cut. The lower chisel head (362) may be similarly connected to a rod (not shown) and to a hammer slide assembly, as needed.

Turning to FIGS. 28A-28D, the tool system also includes an inserter assembly (414) for inserting the prosthetic disc between the vertebral bodies.

Figure 28A:
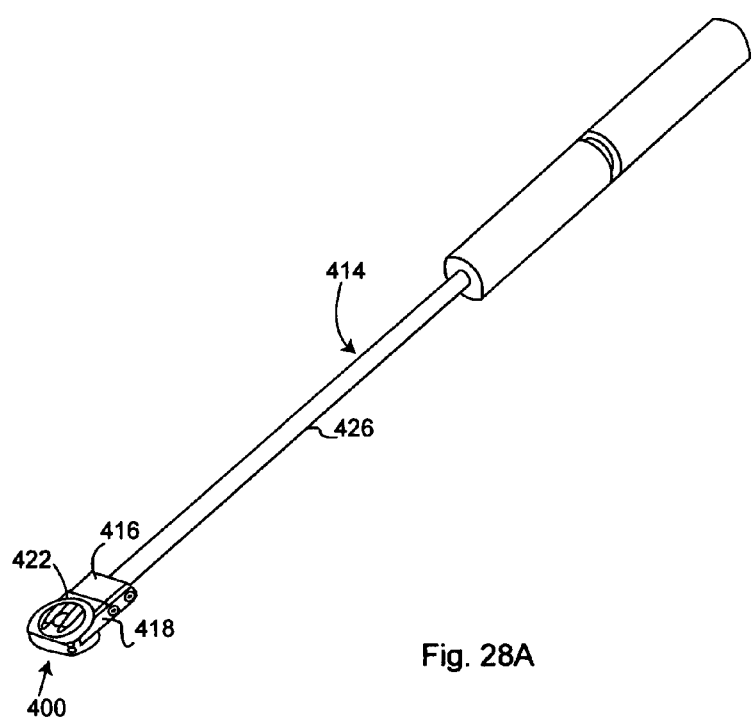
FIG. 28A provides a perspective view of an inserter with a prosthetic disc.

FIG. 28A shows an inserter assembly (414) having an inserter head portion (416) for grasping a prosthetic disc (400) using grasping arms (418a, 418b).

Figure 28B:
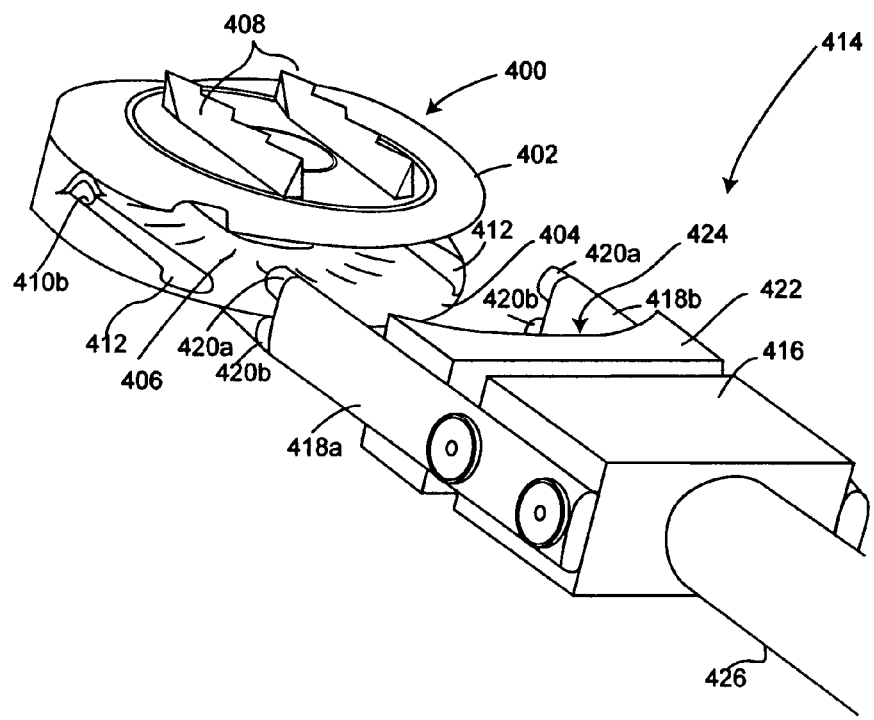
FIG. 28B provides a perspective view of the inserter with the prosthetic disc released showing a relationship between openings in the disc and engagement pins on the inserter.

FIG. 28B shows a prosthetic disc (400) as may be found on the distal end of the inserter assembly (414). The prosthetic disc (400) includes an upper end plate (402), a lower end plate (404), a compressible core member (406) between the upper and lower end plates (402, 404), and anchor fins (408) extending from the upper and lower end plates (402, 404). The prosthetic disc (400) further includes openings (410a, 410b) in the upper and lower end plates (402, 404), respectively.

Figure 28C:
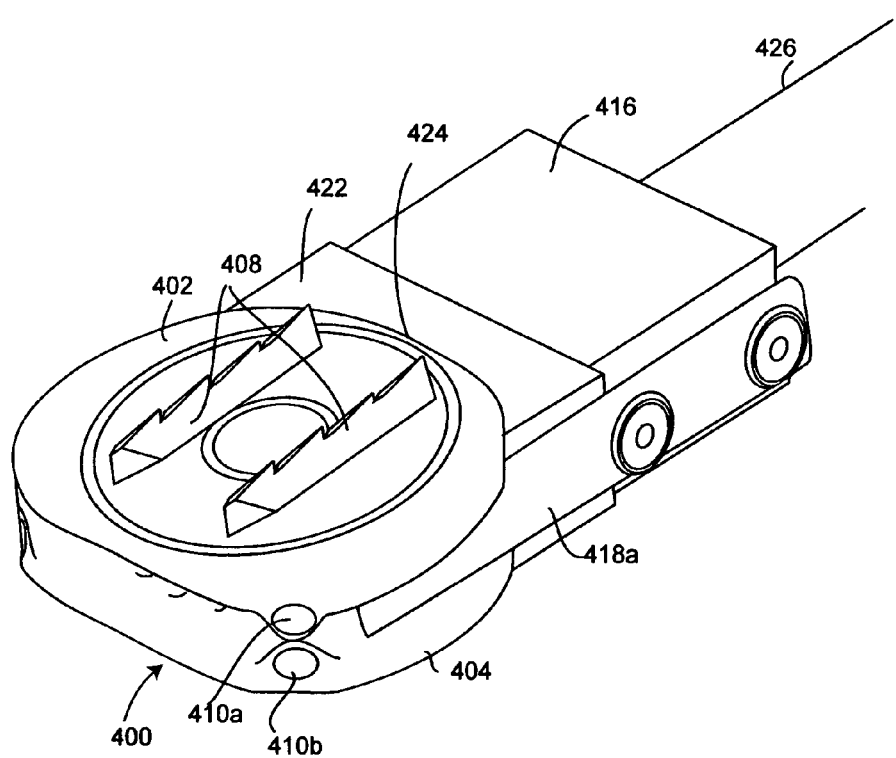
FIG. 28C provides a perspective view of the inserter with the prosthetic disc.

The inserter (414) includes a head portion (416) and two arms (418a, 418b) extending from opposite sides of the head portion (416). Each arm (418a, 418b) includes two engagement pins (420a, 420b) that are to be inserted into the openings (410a, 410b) of the prosthetic disc (400), respectively. The end plates (402, 404) of the prosthetic disc (400) include grooves (412) for allowing the engagement pins (420a, 420b) to pass between the end plates (402, 404) to the openings (410a, 410b), examples of which are shown in FIG. 28C. The inserter (414) further includes a movable pusher (422) that is moveable relative to the head portion (416). The movable pusher (422) has a curved surface (424) corresponding to the shape of the prosthetic disc (400) for receiving the prosthetic disc (400). The head portion (416) of the inserter is connected to a handle (426). The movable pusher (422) may be pushed by an inner rod that slides within the handle (not shown) and is attached to a knob or grip accessible to the surgeon.

Figure 28D:
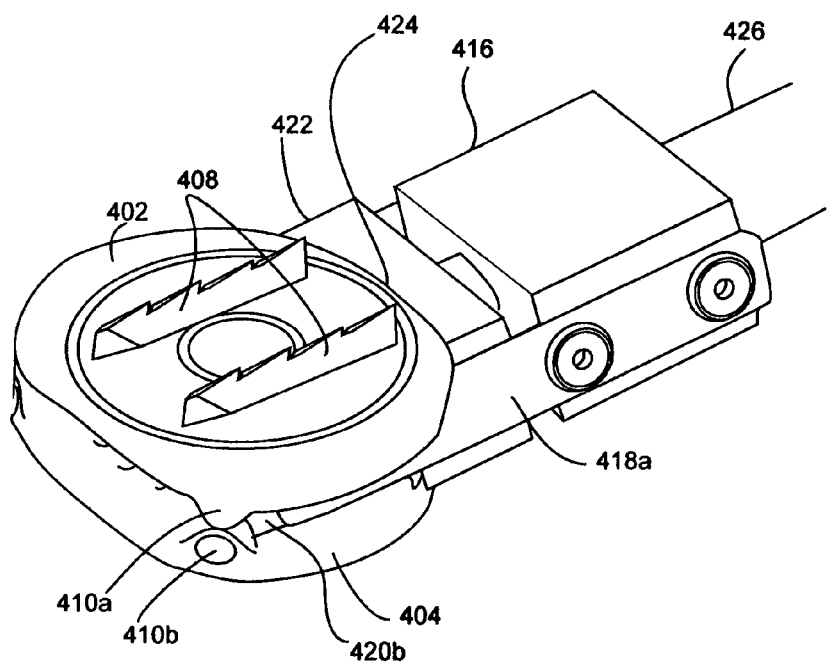
FIG. 28D provides a perspective view of the inserter with the prosthetic being released from the inserter.

To hold the prosthetic disc (400) in the inserter (414), the engagement pins (420a, 420b) of the inserter (414) are inserted into the openings (410a, 410b) of the prosthetic disc (400) through grooves (412). Openings (410a, 410b) and engagement pins (420a, 420b) may be arranged such that the distal end of the prosthetic disc (400) must be compressed to allow pins (420a, 420b) to enter openings (410a, 410b). Said another way: as is shown in FIG. 28D, the prosthetic disc (400) must be into a compressed, hyper-lordotic state when held in the inserter (414), where the hyper-lordotic angle is greater than the lordotic angle between the adjacent vertebral bodies that are to support the prosthetic disc, by 0°-10° and more practically by 3°-7°. The hyper-lordotic angle of the compressed trial facilitates passage of the disc (400) into the disc space located between the vertebral bodies. Clearly, the device may be used to compress the disc (400) to a lordotic angle as well.

Turning to FIGS. 29A-29E, the tool system may include a compression vise (428) for compressing and holding the prosthetic disc (400) in place to facilitate placement of the prosthetic disc (400) in the inserter (414).

Figure 29A:
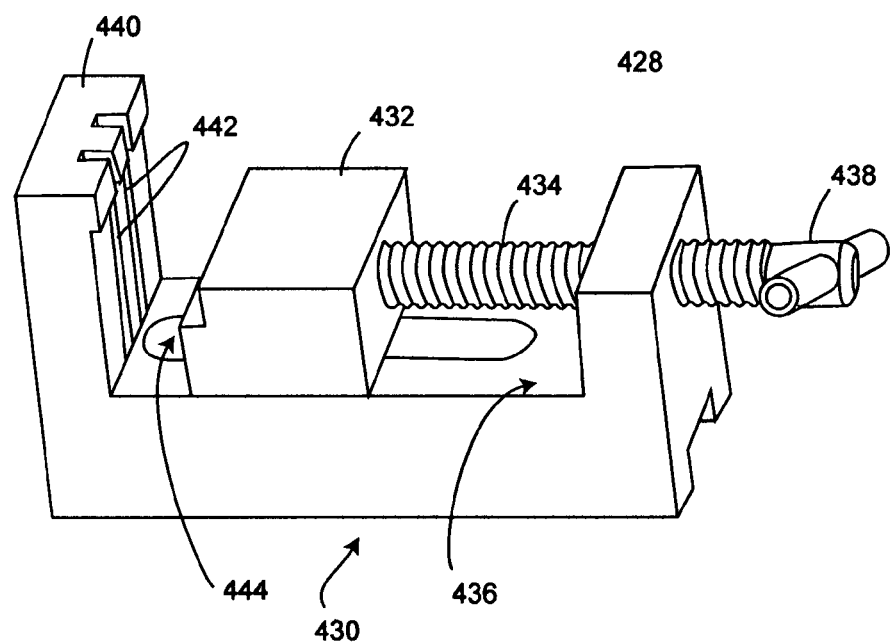
FIG. 29A provides a perspective view of a compression vise for compressing and holding the prosthetic disc for placement in the inserter.

FIG. 29A shows such a compression vise (428) that includes a main body (430), a movable block (432) able to move along a surface (436) of the main body (430), and a lead screw (434) for providing controlled movement of the block (432) along the surface (436) of the main body (430). The lead screw (434) is threaded through a portion of the main body (430) and is connected at one end to the moveable block (432) and at the other end to a T-handle (438). Turning the T-handle (438) moves the moveable block (432) along the surface (436) of the main body (430). The main body (430) includes a fixed block portion (440) that cooperates with the moveable block (432) to compress and to hold the prosthetic disc (400). The fixed block (440) and moveable block (432) include grooves (442) for accommodating the anchor fins (408) of the prosthetic disc (400). This version of the moveable block (432) also includes a stepped surface (444) for compressing the prosthetic disc (400) at a hyper-lordotic angle.

Figure 29B:
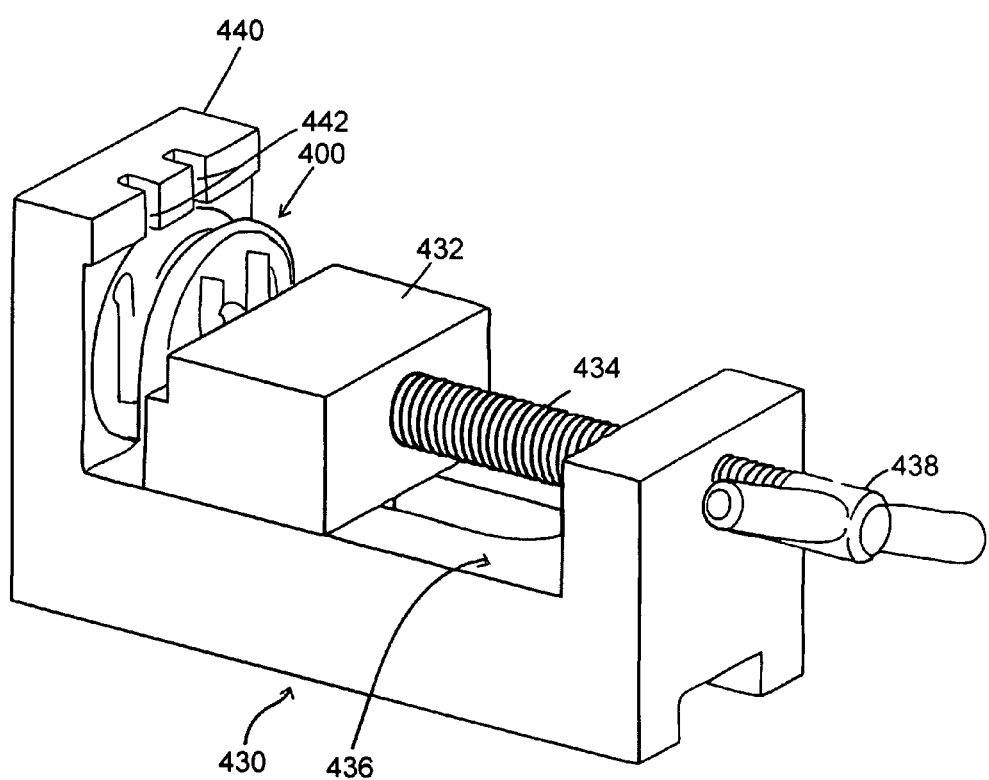
FIG. 29B provides a perspective view of the prosthetic disc in the compression vise in an uncompressed state.
Figure 29C:
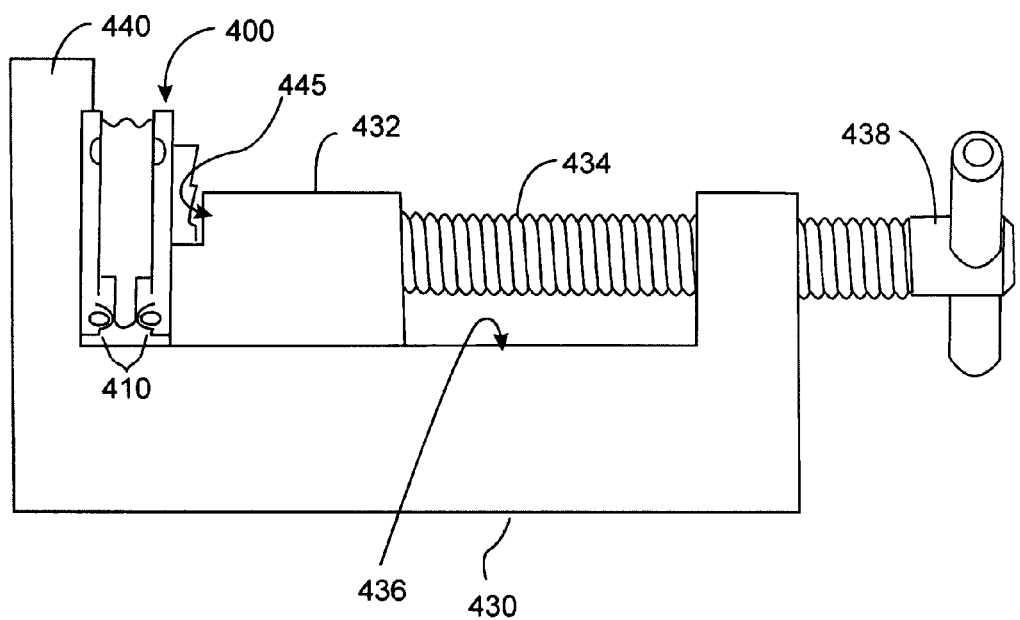
FIG. 29C provides a side view of the prosthetic disc in the compression vise in the uncompressed state.

FIGS. 29B and 29C show, respectively, in perspective and in side view, a prosthetic disc (400) inserted between the fixed block (440) and the movable block (432) but in an uncompressed state.

Figure 29D:
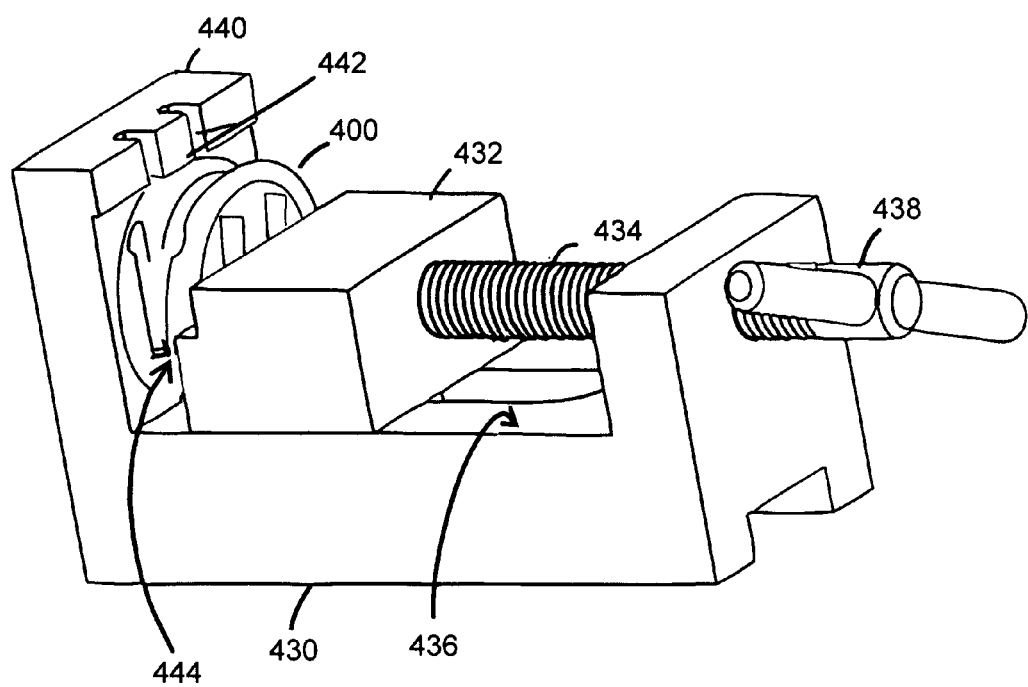
FIG. 29D provides a perspective view of the prosthetic disc in the compression vise in a compressed, hyper-lordotic state.
Figure 29E:
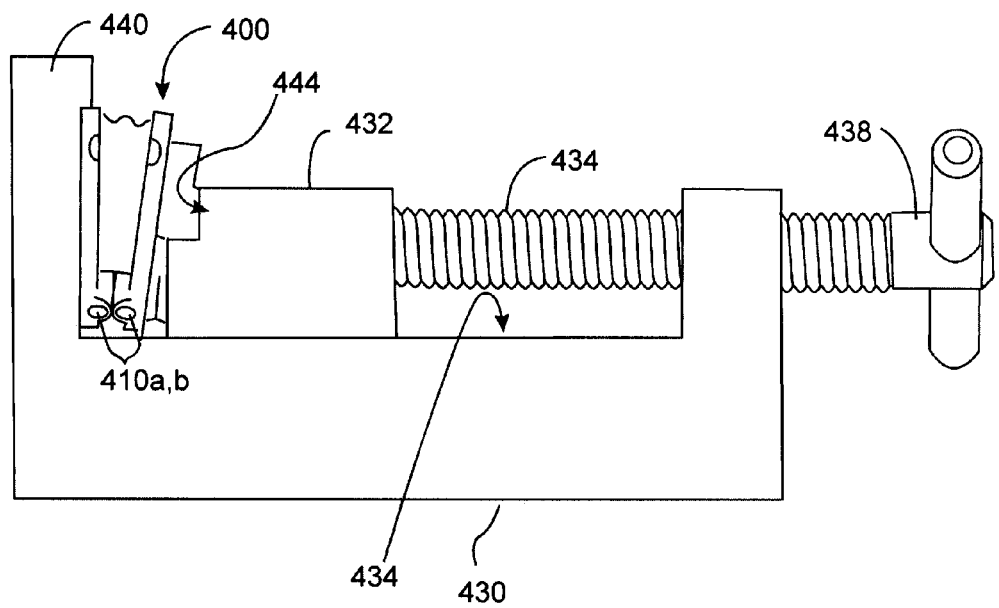
FIG. 29E provides a side view of the prosthetic disc in the compression vise in the compressed, hyper-lordotic state.
Figure 30:
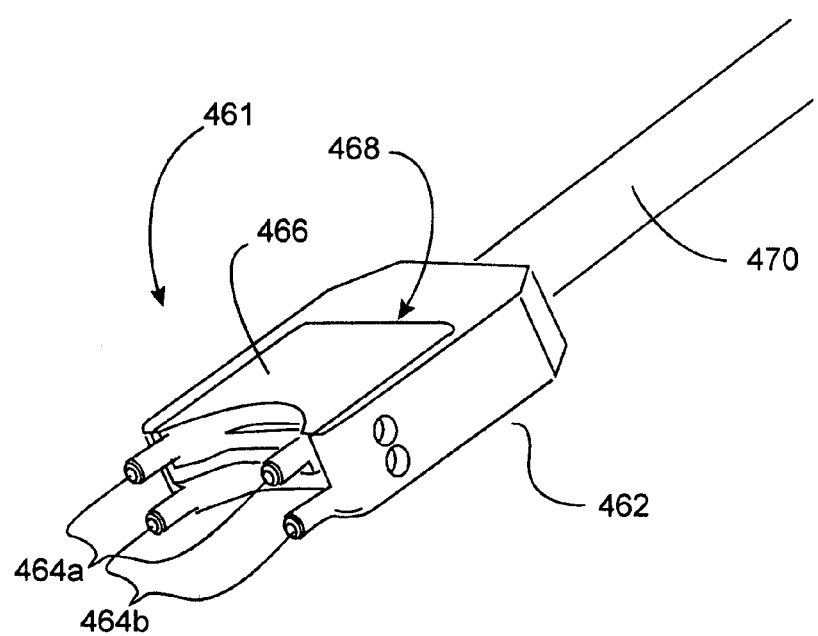
FIG. 30 provides a perspective view of an inserter.
Figure 31:
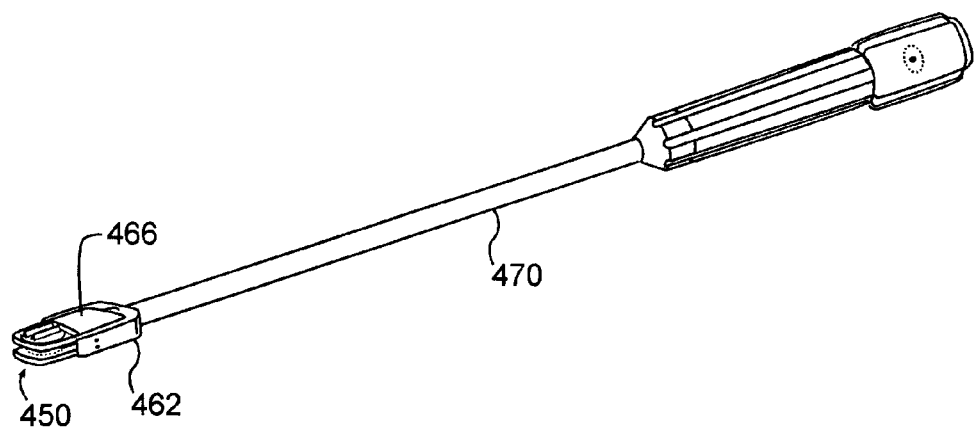
FIG. 31 provides a perspective view of the inserter with a prosthetic intervertebral disc.

FIGS. 29D and 29E show, respectively, in perspective and in side view, a prosthetic disc (400) in a compressed state after the moveable block (432) has been moved forward. The stepped surface (444) of the movable block (432) compresses the prosthetic disc (400) at a hyper-lordotic angle. The prosthetic disc (400) is compressed until that the openings (410a, 410b) of the prosthetic disc (400) align with the engagement pins (420a, 420b) of the inserter (414) for placement of the prosthetic disc (400) in the inserter (414).

FIGS. 30-36 show another inserter variation and a variant of the prosthetic disc. This inserter (461) has the ability to compress the prosthetic disc (450) into the hyper-lordotic state without a vise.

Inserter (461) includes a head portion (462) and a rotatable member (466) that fits into a recess (468) in the head portion (462) and can rotate relative to the head portion (462). The inserter (461) further includes two engagement pins (464b) attached to the head portion (462) and two engagement pins (464a) attached to the rotatable member (466). Both the head portion (462) and the rotatable member (466) have a curved surface corresponding to the shape of the prosthetic disc to be received in the inserter.

Figure 34:
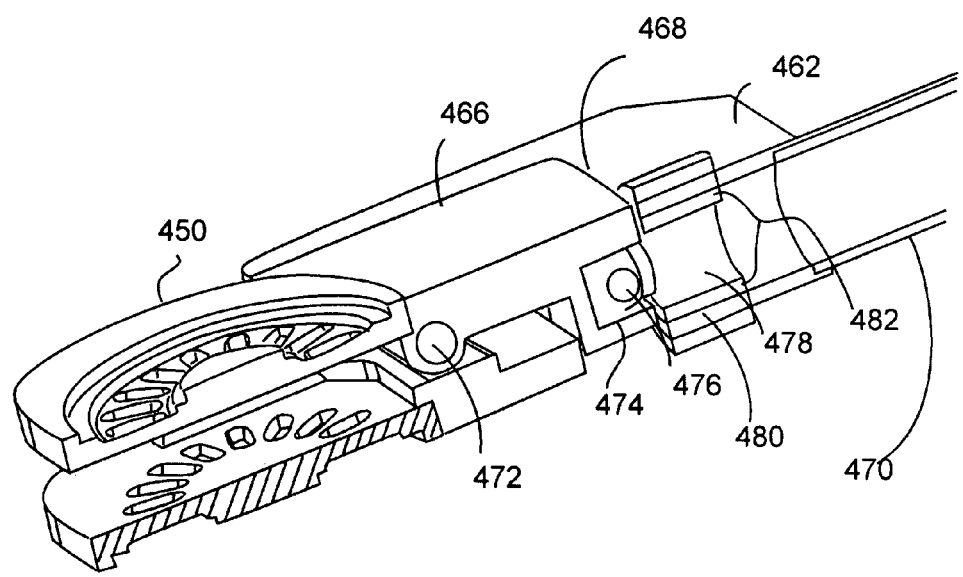
FIG. 34 provides a cross-sectional perspective view of the inserter shown in FIG. 30 showing a cam drive in the inserter for rotating a rotatable member of the inserter.
Figure 35:
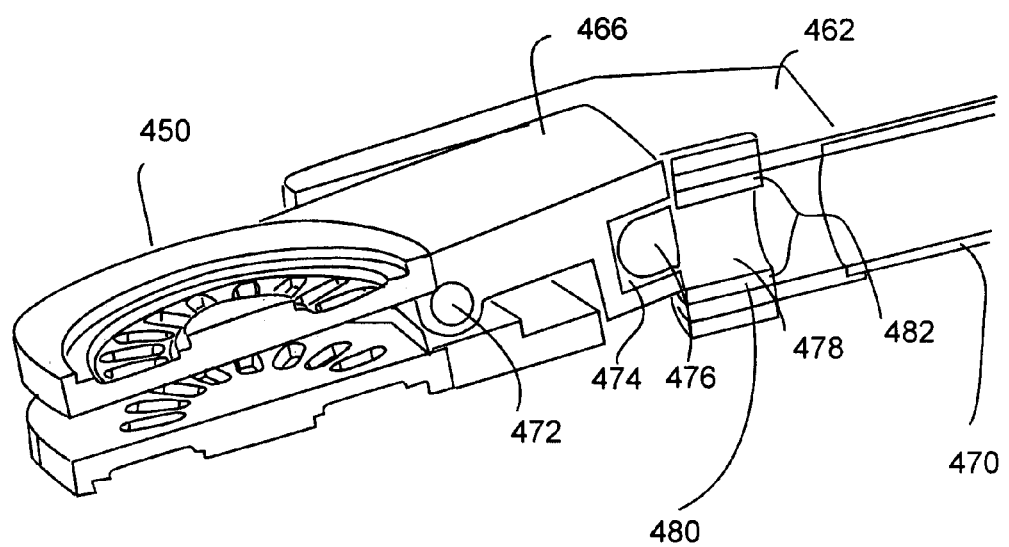
FIG. 35 provides a cross-section perspective view of the inserter shown in FIG. 6, in which the rotatable member is rotated by a cam drive to compress a prosthetic disc to a hyper lordotic state.
Figure 36:
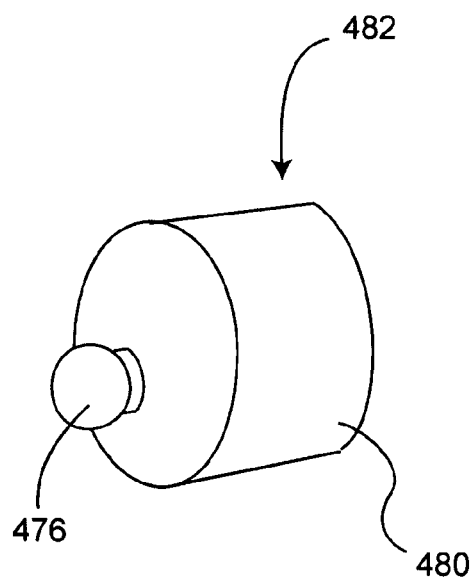
FIG. 36 provides a perspective view of the cam drive.

FIG. 34 shows a cross-sectional view of the inserter (461) holding a "stripped down" version of the prosthetic disc (450). The rotatable member (466) is pivotally connected to the head portion (462) about axis (472). The inserter further includes a cam drive (482) comprising a barrel (480) with a ball (476) protruding from the barrel (480), as shown in isolation in FIG. 36. The ball (476) is positioned off center on the barrel (470) such that rotation of the barrel (470) causes the ball (476) to move up or down. Returning to FIG. 34, the barrel (480) is received in a cylindrical inner compartment (478) of the head portion (462) (barrel (480) is not shown in FIG. 34). The protruding ball (476) is received within an inner compartment (474) of the rotatable member (466). When the barrel (480) is rotated, the ball (476) moves up or down causing the rotatable member (466) to rotate about axis (472). The barrel (480) may be rotated by a rod that runs through the handle of the inserter and is connected at one end to the barrel (480) and at the other end to a knob on the end of the handle.

Figure 32:
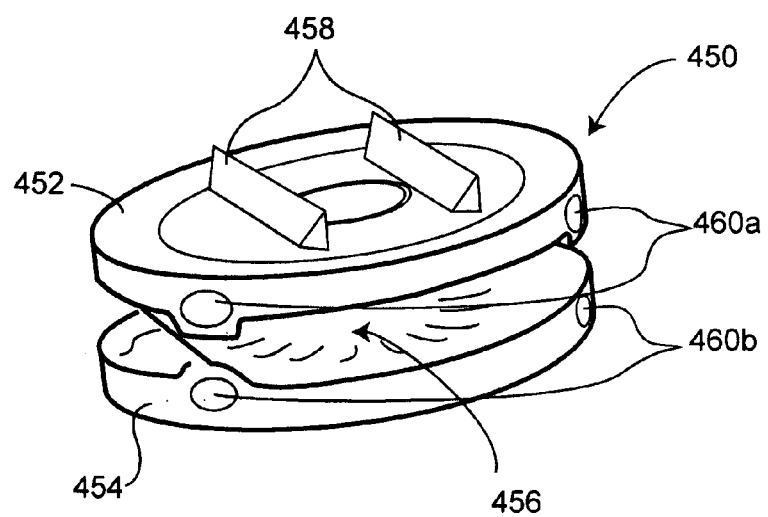
FIG. 32 provides a perspective view of the prosthetic intervertebral disc.

FIG. 32 shows a example of a variation of a prosthetic disc (450) that may be implanted using the inserter (461) otherwise shown in FIGS. 30-35. The depicted prosthetic (450) disc includes an upper end plate (452), a lower end plate (454), and a region (456) for placement of a compressible core member (not shown) between the upper end plate (452) and lower end plate (454). The prosthetic disc (450) also includes anchor fins (458) extending from each of the upper end plate (452) and lower end plate (454).

Figure 33:
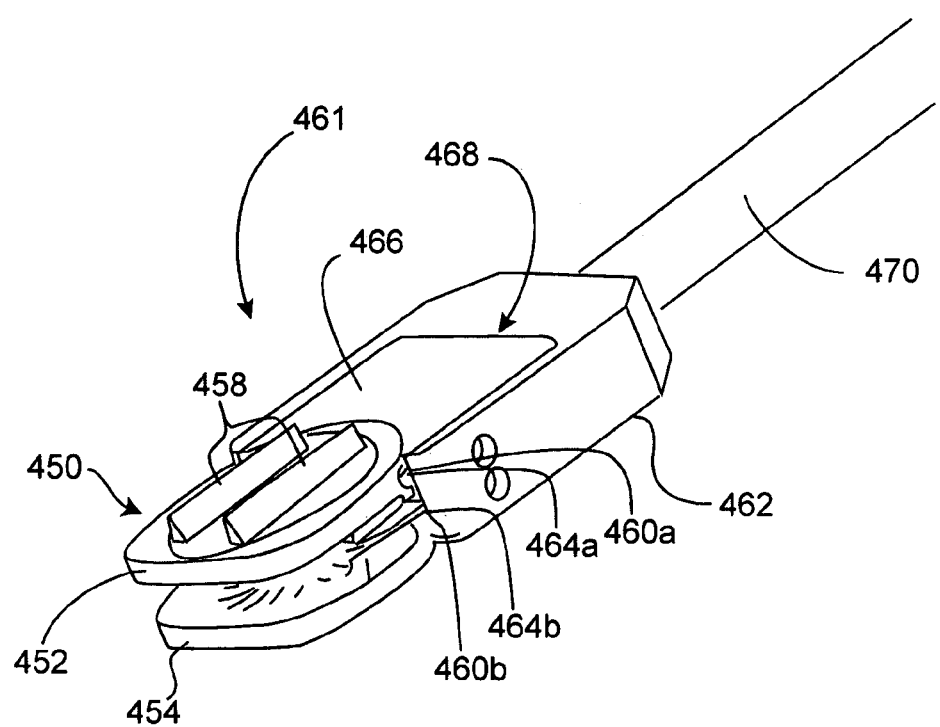
FIG. 33 provides a perspective view of the inserter with the prosthetic intervertebral disc.

FIG. 33 shows the prosthetic disc (450) placed in the inserter (461) by inserting the engagement pins (464a, 464b) of the inserter (461) into the openings (460a, 464b) of the prosthetic disc (450). In this variation, the openings (460a, 464b) are located at the proximal end of the prosthetic disc (450). When prosthetic disc (450) is initially placed on the inserter (461), the rotatable member (466) is substantially parallel to the head portion (462). The rotatable member (466) may then be rotated about axis (472), passing side-to-side using the cam drive (482), as was explained with regard to FIG. 35. Such a rotation causes the pins (464a, 464b) to compress the prosthetic disc (450) into a hyper-lordotic state. The prosthetic disc (450) may then be inserted into the disc space between the vertebral bodies using the inserter (461). After the prosthetic disc (450) is appropriately positioned in the disc space, the prosthetic disc (450) is released by returning the rotatable member back to the position in FIG. 34 to uncompress the disc from the hyper-lordotic state and then withdrawing the inserter (461).

Implantation Procedure

Described below is a typical implantation procedure using the distractor, trials, chisels, and inserter.

An initial step of the procedure is to expose the two vertebrae to be treated using conventional surgical procedures and to remove the natural disc between the vertebrae. The centerline of the vertebral bodies is determined and marked on the anterior surfaces of those vertebral bodies.

The next step is to distract, with the distractor as shown in FIG. 2, the vertebral bodies to create the disc space into which the prosthetic disc will be implanted. The natural lordotic angle between the vertebral bodies is approximated and a distractor lower jaw having the closest lordotic angle is attached to the distractor. The lower jaw having the closest angle may be determined by trial-and-error.

The distractor forks (120, 122) are then inserted between the vertebral bodies. The centerline mark (124) on the distractor is aligned with the centerline marks on the vertebral bodies to ensure that the distractor forks (120, 122) are centered with the vertebral bodies. Proper centering is important because the position of the distractor forks (120, 122) will determine the lateral position of the trial, and the prosthetic disc, in the disc space.

The distractor forks (120, 122) are inserted between the vertebral bodies, centered with the vertebral bodies, and opened by squeezing the distractor levers (118a, 118b). As the forks (120, 122) open, they engage respective surfaces on the superior and inferior vertebral bodies. The forks (120, 122) are opened to achieve a desired distraction height between the vertebral bodies. The roughened surfaces of the forks (120, 122) provide traction between the forks and the vertebral bodies.

As the vertebral bodies are being distracted to create the disc space, a trial (252 in FIGS. 13 and 14) is inserted into the disc space to determine the proper size and position of the prosthetic disc to be implanted. The lordotic angle of the trial may be chosen based on the lordotic angle of the distractor. The trial (252) is inserted into the disc space between the distractor forks (120, 122). This may be done by aligning the trial recesses (256, 260) with the distractor forks (120, 122) and pushing the trial (252) into the disc space. FIG. 23 shows the trial (252) inserted between the distractor forks (120, 122) with the forks (120, 122) fitting into the recesses (256, 258) of the trial (252).

After the trial (252) is inserted into the disc space, the adjustable stop (266 in FIG. 13) is butted against the anterior surfaces of the vertebral bodies. The AP depth of the trial (252) in the disc space is then adjusted by moving the disc portion (254) of the trial relative to the adjustable stop (266).

The AP depth of the disc portion (254) is adjusted by turning handle (280 in FIG. 13.

The position of the disc portion (254) in the disc space may then be fluoroscopically visualized using the radio-opaque pins (288a, 288b, and 288c) in the disc portion (254). Often, the proper depth may be when the trial is seated approximately 1 mm from the posterior aspect of the vertebral body. In some versions of our device, the quick release handle (280) may be detached so not to interfere with fluoroscopy. If the trial (252) is not of the proper size, then the trial (252) can be removed and another trial (252) inserted.

For each lordotic angle, there may be a set of trials of different heights, lengths, and widths. The height of the trial is preferably selected to approximate the height of the patient's healthy natural disc. Examples of heights include 10 mm, 12 mm, and 14 mm.

The selection of trial size depends on a number of factors, including anterior to posterior length and lateral coverage of the vertebrae end plate.

Once the selected and inserted trial matches the prosthetic disc to be implanted with respect to lordosis angle, height, and footprint (AP and lateral coverage), the trial is considered to be appropriately positioned in the disc space and that position is also considered to be position of the prosthetic disc to be implanted.

The handle (280) is then detached from the trial (252) and the distractor is removed leaving the disc portion (254) of the trial (252) in the disc space. Grooves are then cut in the respective surfaces of the adjacent vertebrae using the chisels. see, FIGS. 26A, 26B, and 26C.

In one variation, the lower chisel head (362) is partially inserted into the lower recesses (260) of the trial (252). The blades (366) of the lower chisel head (362) are then driven into the upper surface of the inferior vertebral body by pounding the handle (374) of the chisel with a hammer. The lower recesses (260) guide the lower chisel head (362) as the blades (366) are driven into the lower vertebral body. The stop flanges (368) on the lower chisel head (362) limit the depth of penetration. This ensures that the grooves are cut at a desired depth in the disc space.

After the lower grooves are cut, the lower chisel head (362) is left in the trial. The upper chisel head (350) is then inserted into the upper recesses (256) of the trial (252) and driven into the lower surface of the superior vertebral body by pounding the chisel handle (374) with a hammer. To prevent potential confusion to the surgeon, the handle of the lower chisel (362) is preferably shorter than the handle of the upper chisel (350). Further, if the handle has a removable portion, that portion may be removed. This ensures that the upper grooves on the superior vertebral body are aligned with the lower grooves on the inferior vertebral body. The stop flanges (358) on the upper chisel head (350) limit how far the blades can be driven into the upper vertebral body by engaging the outer proximal surface of the disc portion (254). This procedure ensures that the grooves are cut at the appropriate places, length, and depth to receive the prosthetic disc.

After the grooves are cut into the vertebral bodies, the chisels (350, 362) are removed from the trial using a slide hammer (376) on each chisel head, an example of which is shown in FIG. 27E.

The prosthetic disc (400) is then prepared for implantation into the disc space. As shown in FIGS. 29B and 29C, an appropriately sized, but uncompressed prosthetic disc (400) is placed in the compression vise (428). After the prosthetic disc (400) is compressed, the disc is mounted in the inserter (414) by inserting engagement pins (420a, 420b) of the inserter (414) into the openings (410a, 410b). After the prosthetic disc (400) is mounted in the inserter (414), the vice's moveable block (432) is relaxed to release the prosthetic disc (400) from the compression vise (428).

When the prosthetic disc (400) is held in the inserter (414), the movable pusher (422) is butted against the head portion (416). The trial (252) is then removed from the disc space and the prosthetic disc (400) is inserted into the disc space. The anchor fins (408) on the prosthetic disc (400) are aligned with the corresponding, previously chiseled grooves in the vertebral bodies. After the prosthetic disc (400) is properly positioned fluoroscopically in the disc space, the prosthetic disc (400) is released from the inserter (414). Release of the disc (400) may be accomplished by moving the moveable pusher (422) forward. This movement causes the pins of the inserter (420a, 420b) to retract from openings (410a, 410b). After the pins (420a, 420b) disengage from openings (410a, 410b), the prosthetic disc (400) decompresses, and the anchor fins (408) move fully into the grooves of the vertebrae affixing the prosthetic disc (400) between the vertebral bodies.

Unless defined otherwise, all technical and scientific terms used herein have the same meaning as commonly understood by one of ordinary skill in the art to which this description pertains.

All patents, patent applications, and other publications mentioned herein are hereby incorporated herein by reference in their entireties. The patents, applications, and publications discussed herein are provided solely for their disclosure prior to the filing date of the present application. The disclosure of such documents is not to be construed as an admission that they are "prior" to any description found here.

It will be appreciated that those skilled in the art will be able to devise various arrangements which, although not explicitly described or shown herein, embody the principles described here and are included within their spirit and scope. Furthermore, all examples and conditional language recited herein are principally intended to aid the reader in understanding the principles and concepts of the devices. Those examples and that language are not to be considered as limitations to any claimed device or procedure.

We claim as our invention:

1. A system for implanting a prosthetic intervertebral disc between two adjacent vertebral bodies, comprising:
   a.) a prosthetic intervertebral disc, said prosthetic disc comprising
      i.) a first end plate;
      ii.) a second end plate;
      iii. a compressible and expandable core member positioned between said first and second end plates wherein the core member is expandable between a smaller dimension and a larger implanted dimension; and
      at least two openings in each one of said first and second end plates, each opening being operative to cooperatively, slidably receive an engagement pin on an inserter and to maintain reception of the engagement pin until sliding removal of the engagement pin from the opening; and
   b.) the inserter for inserting said prosthetic disc between said adjacent vertebral bodies, said inserter comprising at least two engagement pins for introduction into the first end plate and at least two engagement pins for introduction into the second plate, each engagement pin slidably insertable into one of the at least two openings in each of the first and second end plates, wherein the engagement pins are cooperatively operative with said openings to release said end plates and to expand the core member from said smaller dimension to said larger implanted dimension upon sliding removal from said openings.

2. The system of claim 1 wherein said engagement pins are arranged on said inserter such that said core member is compressed to said smaller dimension when the prosthetic disc is received in said inserter.

3. The system of claim 2 wherein said prosthetic disc as implanted includes a lordotic angle and said openings are arranged on said first and second end plates such that said prosthetic disc is in a hyper-lordotic state when received in said inserter.

4. The system of claim 2 further comprising a compression vise operative to compress the prosthetic disc such that said core member is compressed to said smaller dimension from a larger dimension and to hold said prosthetic disc in compression for placement in said inserter.

5. The system of claim 1 wherein said inserter comprises:
   a.) a head portion, wherein said engagement pins are fixed relative to said head portion; and
   b.) a movable pusher operative to be movable relative to said head portion, to slidably remove the engagement pins from the openings in the first and second end plates, and thereby to push said prosthetic disc from said inserter.

6. The system of claim 1 wherein said inserter comprises:
   a head portion, wherein at least one of said engagement pins is fixed relative to said head portion; and
   a movable pusher, wherein said movable pusher is operative to be movable relative to said head portion and to push said prosthetic disc from said inserter and wherein at least one of said engagement pins is fixed relative to said movable pusher.

7. A system for implanting a prosthetic intervertebral disc into an intervertebral space between two adjacent vertebral bodies, comprising:
   a.) a prosthetic intervertebral disc, said prosthetic disc having an anterior end and a posterior end, wherein upon implantation of the prosthetic disc into an intervertebral space, the posterior end is initially inserted into the intervertebral space, and the anterior end is operative to receive engagement pins from an inserter, the prosthetic intervertebral disc comprising:
      i.) a first end plate including at least two passageways extending from the anterior end towards the posterior end, each said passageway operative to receive an engagement pin from the inserter;
      ii.) a second end plate including at least two passageways extending from the anterior end towards the posterior end, each said passageway operative to receive an engagement pin from the inserter; and
      iii.) a compressible and expandable core member positioned between said first and second end plates, the compressible core member being operative to be compressed from a larger dimension to a smaller dimension when the first end plate is moved towards the second end plate and the engagement pins are received into said passageways; and wherein the core member expands from said smaller dimension to a larger implanted dimension when the engagement pins are slidably removed from said passageways; and
   b.) the inserter for inserting said prosthetic disc between said adjacent vertebral bodies, said inserter comprising at least two engagement pins for each of the first end plate and the second end plate, wherein each engagement pin is operative to be received in one of said passageways and wherein the a at least two engagement pins are operative to release said prosthetic disc from the inserter and to allow the core member to expand from said smaller dimension and to said larger implanted dimension upon sliding removal of the plurality of engagement pins from the respective passageways.

8. The system of claim 7 wherein said engagement pins are arranged on said inserter such that said core member is compressed to said smaller dimension when the prosthetic disc is received in said inserter.

9. The system of claim 8 wherein said prosthetic disc as implanted includes a lordotic angle and said passageways are arranged on said first and second end plates such that said prosthetic disc is in a hyper-lordotic state when received in said inserter.

10. The system of claim 8 further comprising a compression vise operative to compress the prosthetic disc such that said core member is compressed to said smaller dimension from a larger dimension and to hold said prosthetic disc in compression for placement in said inserter.

11. The system of claim 7 wherein said inserter comprises:
   a.) a head portion, wherein said engagement pins are fixed relative to said head portion; and
   b.) a movable pusher operative to be movable relative to said head portion, to slidably remove the engagement pins from the openings in the first and second end plates, and thereby to push said prosthetic disc from said inserter.

12. The system of claim 7 wherein said inserter comprises:
   a.) a head portion, wherein at least one of said engagement pins is fixed relative to said head portion; and b.) a movable pusher, wherein said movable pusher is operative to be movable relative to said head portion and to push said prosthetic disc from said inserter and wherein at least one of said engagement pins is fixed relative to said movable pusher.

13. A system for implanting a prosthetic intervertebral disc between two adjacent vertebral bodies, comprising:
   a.) a prosthetic intervertebral disc, said prosthetic disc comprising
      i.) a first end plate having at least two passageways and an opening to each of said at least two passageways one passageway, each of the at least two passageways having a closed wall, the openings and passageways each being operative to cooperatively, slidably receive an engagement pin on an inserter and to maintain reception of the engagement pin until sliding removal of the engagement pin from the opening and the passageway;
      ii.) a second end plate having at least two passageways and an opening to each of said at least two passageways, each of the at least two passageways having a closed wall, the openings and passageways each being operative to cooperatively, slidably receive an engagement pin on an inserter and to maintain reception of the engagement pin until sliding removal of the engagement pin from the opening and the passageway;
      iii.) a compressible core member positioned between said first and second end plates; and
   b.) the inserter for inserting said prosthetic disc between said adjacent vertebral bodies, said inserter comprising engagement pins each slidably insertable into one of the openings in each of the first and second end plates, wherein the engagement pins are cooperatively operative to release said end plates upon sliding removal from said openings and said passageways; and wherein said engagement pins are arranged on said inserter such that said core member is compressed to a smaller dimension when the prosthetic disc is received in said inserter, said core member having a larger implantation dimension when said prosthetic disc is implanted between said two adjacent vertebral bodies.

14. The system of claim 13 wherein said prosthetic disc as implanted includes a lordotic angle and said openings are arranged on said first and second end plates such that said prosthetic disc is in a hyper-lordotic state when received in said inserter.

15. The system claim 13 further comprising a compression vise operative to compress the prosthetic disc such that said core member is compressed to said smaller dimension from a larger dimension and to hold said prosthetic disc in compression for placement in said inserter.

16. The system of claim 13 wherein said inserter comprises:
   a.) a head portion, wherein said engagement pins are fixed relative to said head portion; and
   b.) a movable pusher operative to be movable relative to said head portion, to slidably remove the engagement pins from the opening and at least one passageway in the first and second end plates, and thereby to push said prosthetic disc from said inserter.

17. The system of claim 13 wherein said inserter comprises:
   a head portion, wherein at least one of said engagement pins is fixed relative to said head portion; and
   a movable pusher, wherein said movable pusher is operative to be movable relative to said head portion and to push said prosthetic disc from said inserter and wherein at least one of said engagement pins is fixed relative to said movable pusher.

18. A system for implanting a prosthetic intervertebral disc into an intervertebral space between two adjacent vertebral bodies, comprising:
   a.) a prosthetic intervertebral disc, said prosthetic disc having an anterior end and a posterior end, wherein upon implantation of the prosthetic disc into intervertebral space, the posterior end is initially inserted into the intervertebral space, and the anterior end is operative to receive engagement pins from an inserter, the prosthetic intervertebral disc comprising:
      i.) a first end plate including at least two passageways extending from the anterior end towards the posterior end, the at least two passageways each passageway operative to receive an engagement pin from the inserter;
      ii.) a second end plate including at least two passageways extending from the anterior end towards the posterior end, the at least two passageways each operative to receive an engagement pin from the inserter; and
      iii.) a compressible and expandable core member positioned between said first and second end plates, the compressible core member being operative to be compressed from a larger dimension to a smaller dimension when the first end plate is moved towards the second end plate and the engagement pins are received into said passageways; and
   b.) the inserter for inserting said prosthetic disc between said adjacent vertebral bodies, said inserter comprising at least two horizontal engagement pins for each of the first end plate and the second end plate, wherein each engagement pin is operative to be received in the anterior end of one of said passageways and wherein the engagement pins are operative to release said prosthetic disc from the inserter and to allow the core member to expand from said smaller dimension to said larger dimension upon sliding removal of the engagement pins from the anterior ends of the respective passageways.

19. The system of claim 18 wherein said engagement pins are arranged on said inserter such that said core member is compressed to the smaller dimension when the prosthetic disc is received in said inserter.

20. The system of claim 19 wherein said prosthetic disc as implanted includes a lordotic angle and said passageways are arranged on said first and second end plates such that said prosthetic disc is in a hyper-lordotic state when received in said inserter.

21. The system of claim 19 further comprising a compression vise operative to compress the prosthetic disc such that said core member is compressed to said smaller dimension from a larger dimension and to hold said prosthetic disc in compression for placement in said inserter.

22. The system of claim 18 wherein said inserter comprises:
   a.) a head portion, wherein said engagement pins are fixed relative to said head portion; and
   b.) a movable pusher operative to be movable relative to said head portion, to slidably remove the engagement pins from the openings in the first and second end plates, and thereby to push said prosthetic disc from said inserter.

23. The system of claim 18 wherein said inserter comprises:
   a.) a head portion, wherein at least one of said engagement pins is fixed relative to said head portion; and
   b.) a movable pusher, wherein said movable pusher is operative to be movable relative to said head portion and to push said prosthetic disc from said inserter and wherein at least one of said engagement pins is fixed relative to said movable pusher.

* * * * *